(12) United States Patent
Vukelic

(10) Patent No.: US 11,666,481 B1
(45) Date of Patent: Jun. 6, 2023

(54) DIAGNOSIS AND TREATMENT OF COLLAGEN-CONTAINING TISSUES

(71) Applicant: The Trustees of Columbia University in the City of New York, New York, NY (US)

(72) Inventor: Sinisa Vukelic, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 513 days.

(21) Appl. No.: 16/192,364

(22) Filed: Nov. 15, 2018

Related U.S. Application Data

(60) Provisional application No. 62/593,525, filed on Dec. 1, 2017.

(51) Int. Cl.
*A61F 9/008* (2006.01)
*A61F 9/009* (2006.01)

(52) U.S. Cl.
CPC .......... *A61F 9/00827* (2013.01); *A61F 9/009* (2013.01); *A61F 9/0084* (2013.01); *A61F 2009/00842* (2013.01); *A61F 2009/00872* (2013.01); *A61F 2009/00882* (2013.01); *A61F 2009/00897* (2013.01)

(58) Field of Classification Search
CPC .... A61F 9/00827; A61F 9/0084; A61F 9/009; A61F 2009/00842; A61F 2009/00897; A61F 2009/00872; A61F 2009/00882
See application file for complete search history.

(56) References Cited

U.S. PATENT DOCUMENTS

| | | | |
|---|---|---|---|
| 4,638,801 | A | 1/1987 | Daly et al. |
| 4,784,135 | A | 11/1988 | Blum et al. |
| 4,840,175 | A | 6/1989 | Peyman |
| 5,334,190 | A | 8/1994 | Seiler |
| 5,556,406 | A | 9/1996 | Gordon et al. |
| 5,720,894 | A | 2/1998 | Neev et al. |
| 5,735,843 | A | 4/1998 | Trokel |
| 5,861,955 | A | 1/1999 | Gordon |
| 6,099,521 | A | 8/2000 | Shadduck |

(Continued)

FOREIGN PATENT DOCUMENTS

| DE | 102010020194 A1 | 11/2011 |
|---|---|---|
| EP | 2283344 A1 | 2/2011 |

(Continued)

OTHER PUBLICATIONS

Turner R, McGaughey, Klitzman, A. Laser Vision Correction: From one Medical student to another. EyeRounds.org. Nov. 29, 2011 (Year: 2011).*

(Continued)

*Primary Examiner* — Gary Jackson
*Assistant Examiner* — Alexander M Eisenberg
(74) *Attorney, Agent, or Firm* — Potomac Law Group, PLLC

(57) ABSTRACT

In various embodiments, a laser is scanned across biological tissue to alter the characteristics of the tissue. To alter the optical characteristics of a cornea, the laser is scanned in an annular pattern over a region having a ratio of the outer diameter of the region to the inner diameter of the region. The laser may also be used to irradiate cartilage in joints to treat osteoarthritis.

27 Claims, 20 Drawing Sheets

(56) References Cited

U.S. PATENT DOCUMENTS

| | | |
|---|---|---|
| 6,110,166 A | 8/2000 | Juhasz |
| 6,146,375 A | 11/2000 | Juhasz et al. |
| 6,161,546 A | 12/2000 | Yavitz |
| 6,511,800 B1 | 1/2003 | Singh |
| 6,648,877 B1 | 11/2003 | Juhasz et al. |
| 6,902,561 B2 | 6/2005 | Kurtz et al. |
| 6,934,576 B2 | 8/2005 | Camacho et al. |
| 7,241,461 B2 | 7/2007 | Myhill et al. |
| 7,413,781 B2 | 8/2008 | Hubbell et al. |
| 7,645,449 B2 | 1/2010 | Stassi et al. |
| 7,729,749 B2 | 6/2010 | Roessler et al. |
| 8,088,124 B2 | 1/2012 | Loesel et al. |
| 8,114,067 B1 | 2/2012 | Ketteridge et al. |
| 8,215,314 B2 | 7/2012 | Chan et al. |
| 8,262,646 B2 | 9/2012 | Frey et al. |
| 8,279,901 B2 | 10/2012 | Karavitis |
| 8,343,142 B2 | 1/2013 | König et al. |
| 8,366,689 B2 | 2/2013 | Marshall et al. |
| 8,409,177 B1 | 4/2013 | Lai |
| 8,523,846 B2 | 9/2013 | Makino |
| 8,528,566 B2 | 9/2013 | Loesel et al. |
| 8,536,207 B2 | 9/2013 | Yoshida et al. |
| 8,545,487 B2 * | 10/2013 | Muller ............ A61B 18/1815 606/5 |
| 8,569,367 B2 | 10/2013 | Vehige et al. |
| 8,585,686 B2 | 11/2013 | Bergt et al. |
| 8,617,147 B2 | 12/2013 | Knox et al. |
| 8,688,199 B2 | 4/2014 | Dudhia et al. |
| 8,784,406 B2 | 7/2014 | Rathjen |
| 8,915,905 B2 | 12/2014 | Vogler et al. |
| 8,974,444 B2 | 3/2015 | Alfano et al. |
| 9,095,414 B2 | 8/2015 | Jester et al. |
| 9,101,446 B2 | 8/2015 | Bor et al. |
| 9,125,599 B2 | 9/2015 | Chen |
| 9,125,856 B1 | 9/2015 | Paik et al. |
| 9,155,652 B2 | 10/2015 | Peyman |
| 9,226,853 B2 | 1/2016 | Bor et al. |
| 9,271,870 B2 | 3/2016 | Palanker et al. |
| 9,504,607 B2 | 11/2016 | Russmann |
| 9,539,143 B2 | 1/2017 | Holliday et al. |
| 9,545,340 B1 | 1/2017 | Knox et al. |
| 9,555,111 B2 | 1/2017 | Rubinfeld et al. |
| 9,622,911 B2 | 4/2017 | Rubinfeld et al. |
| 9,622,912 B2 | 4/2017 | Knox et al. |
| 9,681,984 B2 | 6/2017 | Peyman |
| 9,695,218 B2 | 7/2017 | Yang et al. |
| 9,814,567 B2 | 11/2017 | Peyman |
| 9,883,970 B2 | 2/2018 | Lopath et al. |
| 10,448,819 B2 | 10/2019 | Weeber |
| 10,940,042 B2 | 3/2021 | Vukelic et al. |
| 2005/0119587 A1 | 6/2005 | Roessler et al. |
| 2005/0129685 A1 | 6/2005 | Cao et al. |
| 2007/0049808 A1 | 3/2007 | Roessler et al. |
| 2007/0213792 A1 | 9/2007 | Yaroslavsky et al. |
| 2008/0031923 A1 | 2/2008 | Murray et al. |
| 2008/0094572 A1 | 4/2008 | Lai |
| 2009/0024117 A1 | 1/2009 | Muller |
| 2009/0171325 A1 | 7/2009 | Koenig |
| 2009/0171327 A1 | 7/2009 | Kurtz et al. |
| 2010/0004643 A1 * | 1/2010 | Frey ............ A61F 9/008 606/5 |
| 2010/0027282 A1 | 2/2010 | Gebauer et al. |
| 2010/0210996 A1 | 8/2010 | Peyman |
| 2010/0216226 A1 | 8/2010 | Hyde et al. |
| 2010/0272824 A1 | 10/2010 | Lupton et al. |
| 2010/0286156 A1 | 11/2010 | Pinelli |
| 2010/0318017 A1 | 12/2010 | Lewis et al. |
| 2011/0077624 A1 | 3/2011 | Brady et al. |
| 2011/0208300 A1 | 8/2011 | de Juan et al. |
| 2012/0078240 A1 | 3/2012 | Spooner |
| 2012/0083772 A1 | 4/2012 | Rubinfeld et al. |
| 2012/0083776 A1 * | 4/2012 | Dai ............ A61F 9/00804 606/5 |
| 2012/0310223 A1 * | 12/2012 | Knox ............ A61F 9/00834 606/5 |
| 2012/0330291 A1 | 12/2012 | Jester et al. |
| 2013/0110091 A1 * | 5/2013 | Berry ............ A61F 9/008 606/5 |
| 2013/0116757 A1 * | 5/2013 | Russmann ............ A61F 9/008 607/89 |
| 2013/0245536 A1 | 9/2013 | Friedman et al. |
| 2013/0245617 A1 | 9/2013 | Rathjen |
| 2013/0267528 A1 | 10/2013 | Pinelli |
| 2013/0338650 A1 * | 12/2013 | Jester ............ A61F 9/008 606/5 |
| 2014/0066835 A1 | 3/2014 | Muller et al. |
| 2014/0114296 A1 * | 4/2014 | Woodley ............ A61B 34/25 606/6 |
| 2014/0155871 A1 | 6/2014 | Cumming |
| 2014/0155872 A1 | 6/2014 | Stevens |
| 2014/0171927 A1 | 6/2014 | Depfenhart |
| 2014/0275935 A1 * | 9/2014 | Walsh ............ A61B 3/0083 600/398 |
| 2015/0032091 A1 | 1/2015 | Teuma et al. |
| 2015/0126921 A1 | 5/2015 | Rubinfeld et al. |
| 2015/0133901 A1 * | 5/2015 | Serdarevic ............ A61F 9/00814 606/5 |
| 2015/0144792 A1 | 5/2015 | Gunn |
| 2015/0202085 A1 | 7/2015 | Lemonis et al. |
| 2015/0305933 A1 | 10/2015 | Zhou |
| 2015/0313756 A1 | 11/2015 | Skerl et al. |
| 2015/0359668 A1 | 12/2015 | Kornfield et al. |
| 2016/0059032 A1 | 3/2016 | Skerl |
| 2016/0081852 A1 * | 3/2016 | Peyman ............ A61F 9/0079 604/20 |
| 2016/0101045 A1 | 4/2016 | Raymond et al. |
| 2016/0106590 A1 | 4/2016 | Bischoff et al. |
| 2016/0136109 A1 | 5/2016 | Isenburg et al. |
| 2016/0151202 A1 | 6/2016 | Scarcelli et al. |
| 2016/0302971 A1 | 10/2016 | Morley et al. |
| 2016/0310319 A1 | 10/2016 | Friedman et al. |
| 2016/0338588 A1 | 11/2016 | Friedman |
| 2016/0374857 A1 | 12/2016 | Fu et al. |
| 2016/0374858 A1 | 12/2016 | Goos et al. |
| 2017/0021021 A1 | 1/2017 | Kamaev et al. |
| 2017/0043015 A1 | 2/2017 | Alageel et al. |
| 2017/0246471 A1 | 8/2017 | Lopath |
| 2017/0319383 A1 | 11/2017 | Luttrull et al. |
| 2018/0021086 A1 | 1/2018 | Deladurantaye et al. |
| 2018/0021172 A1 | 1/2018 | Zheleznyak et al. |
| 2018/0050104 A1 | 2/2018 | Xie et al. |
| 2018/0160898 A1 | 6/2018 | Yoo et al. |
| 2018/0177550 A1 | 6/2018 | Anderson et al. |
| 2018/0221201 A1 | 8/2018 | Vukelic et al. |
| 2021/0187165 A1 | 6/2021 | Vukelic et al. |

FOREIGN PATENT DOCUMENTS

| | | |
|---|---|---|
| EP | 1742311 B1 | 3/2011 |
| EP | 2872082 B1 | 9/2020 |
| WO | 1998005279 A1 | 2/1998 |
| WO | 2000074648 A2 | 12/2000 |
| WO | 2006061565 A1 | 6/2006 |
| WO | 2009073600 A1 | 6/2009 |
| WO | 2011046236 A9 | 7/2011 |
| WO | 2012145159 A1 | 10/2012 |
| WO | 2014065863 A1 | 5/2014 |
| WO | 2014159691 A1 | 10/2014 |
| WO | 2014210152 A2 | 12/2014 |
| WO | 2015010119 A2 | 1/2015 |
| WO | 2015138786 A1 | 9/2015 |
| WO | 2015162559 A1 | 10/2015 |
| WO | 2015138794 A9 | 3/2016 |
| WO | 2016100411 A2 | 6/2016 |
| WO | 2017031167 A1 | 2/2017 |
| WO | 2017070637 A1 | 4/2017 |
| WO | 2018119453 A1 | 6/2018 |

(56) References Cited

OTHER PUBLICATIONS

International Search Report and Written Opinion dated Jun. 11, 2019 for International Patent Application No. PCT/US2019/024321.
Ricard-Blum et al.; "Collagen Cross-Linking"; Int. J. Biochem, vol. 21, No. 11, pp. 1185-1189; Apr. 27, 1989.
Rich et al.; "The Molecular Structure of Collagen"; J. Mol. Biol. (1961) 3; pp. 483-506; Feb. 23, 1961.
Rocha et al., "Comparative study of riboflavin-UVA cross-linking and "flash-linking" using surface wave elastometry," Journal of Refractive Surgery, Sep. 1, 2008, vol. 24(7), pp. S748-S751.
Romero-Jimenez, M., et al "Keratoconus: a review. Contact Lens and Anterior Eye," 33(4), 157-166 (2010).
S. Turunen et al, "Pico- and femtosecond laser-induced crosslinking of protein microstructures: evaluation of processability and bioactivity", 2011 Biofabrication 3 045002 (http://iopscience.iop.org/1758-5090/3/4/045002), downloaded Oct. 9, 2011, pp. 1-14.
Saarakkala et al., "Specificity of Fourier Transform Infrared (FTIR) microspectroscopy to estimate depth wise proteoglycan content in normal and osteoarthritic human articular cartilage" Cartilage, Oct. 2010, 1 (4), pp. 262-269.
Sagoo et al 2004; "Inflammatory Cytokines Induce Apoptosis of Corneal Endothelium through Nitric Oxide" Investigative Ophthalmology & Visual Science Nov. 2004, vol. 45, 3964 3973. doi:10.1167/iovs.04-0439.
Sakimoto T, Rosenblatt MI, Azar DT. Laser eye surgery for refractive errors. The Lancet Apr. 2006; 367(9520): pp. 1432-1447.
Salomão MQ1, et al "Corneal wound healing after ultraviolet-A/riboflavin collagen cross-linking: a rabbit study" J Refract Surg. Jun. 2011;27(6):401-7. doi: 10.3928/1081597X-20101201-02. Epub Dec. 1, 2010.
Schumachers, et al "Absorption of UV-light by riboflavin solutions with different concentration."; J Refract Surg. 2012;28:91-92.
Sidhu et al., "Femtosecond laser-assisted selective reduction of neovascularization in rat cornea," Lasers in Medical Science, Jul. 1, 2014, vol. 29(4), pp. 1417-1427.
Singh, A., et al "Possible formation of singlet oxygen from vibrationally excited water," Journal of Photochemistry, 25(2), 99-104(1984).
Søndergaard AP, et al. "Corneal distribution of riboflavin prior to collagen cross-linking"; Current Eye Research. 2010;35:116-121.
Sorkin et al., "Corneal Collagen Crosslinking: A Systematic Review," Ophthalmologica, vol. 232, pp. 10-27, Apr. 2014.
Spoerl et al., "Corneal Cross-Linking and Safety Issues," The Open Ophthalmology Journal, vol. 5, pp. 14-16, Feb. 2011.
Spoerl et al., "Induction of cross-links in corneal tissue", Experimental Eye Research, Jan. 1, 1998, vol. 66(1), pp. 97-103.
Spoerl, E., et al "Thermomechanical behavior of collagen-cross-linked porcine cornea," Ophthalmologica, 218(2), 136-140 (2004).
Takahashi, Y., et al "Raman spectroscopy investigation of load-assisted microstructural alterations in human knee cartilage: Preliminary study into diagnostic potential for osteoarthritis" Journal of the Mechanical Behavior of Biomedical Materials vol. 31pp. 77-86Mar. 4, 2014.
Turunen et al; "Pico- and femtosecond laser-induced crosslinking of protein microstructures: evaluation of processability and bioactivity"; Biofabrication 3 (2011) 045002 (14pp).
Vaddavalli et al., "Air bubble in anterior chamber as indicator of full-thickness incisions in femtosecond-assisted astigmatic keratotomy," Journal of Cataract & Refractive Surgery, Sep. 1, 2011, vol. 37(9), pp. 1723-1725.
Vazirani et al., "Keratoconus: current perspectives," Clinical Ophthalmology, vol. 7, pp. 2019-2030, Oct. 2013.
Vinciguerra P, et al. "Corneal collagen crosslinking for ectasia after excimer laser refractive surgery: 1-year results." J Refract Surg. 2010;26:486-497.
Vogel et al, "Low-Density Plasma Below the Optical Breakdown Threshold—Potential Hazard for Multiphoton Microscopy, and a Tool for the Manipulation of Intracellular Events", Proc. SPIE vol. 4620, Multiphoton Microscopy in the Biomedical Sciences II, 2002, 15 pages.

Vukelic et al., "Investigation of the morphology of the features generated via femtosecond lasers in the interior of a bovine cornea sections", SPIE Proceedings vol. 8579, Optical Interactions with Tissue and Cells XXIV, 857904, Feb. 15, 2013. 10 pages.
Vukelic et al.; "Ultrafast Laser Induced Structural Modification of Fused Silica—Part II: Spatially Resolved and Decomposed Raman Spectral Analysis"; Journal of Manufacturing Science and Engineering; 132; No. 6:061013; 2010.
Wang C, et al "Quantitative analysis of Raman spectra for assessment of cross link concentrations toward diagnosing early osteoarthritis." Summer Biomechanics, Bioengineering and Biotransport Conference. Snowbird UT, USA (2015).
Wang C., et al "Femtosecond Laser Irradiation as Novel Paradigm for Treatment of Early Osteoarthritis," Annual Meeting of the Orthopaedic Research Society. San Diego, CA, USA (2017).
Wang et al.;"A New Paradigm for Use of Ultrafast Lasers in Ophthalmology for Enhancement of Corneal Mechanical Properties and Permanent Correction of Refractive Errors"; Proc. of SPIE vol. 10066; Energy-based Treatment of Tissue and Assessment IX, 100660Y. Feb. 2017.
Wang, C., et al "Near-infrared Femtosecond Laser as a potential Tool for non-invasive Refractive Error Corrections," In preparation (2017).
Wang, C., et al "Quantitative Raman characterization of cross-linked collagen thin films as a model system for diagnosing early osteoarthritis," SPIE BiOS, International Society for Optics and Photonics, 970415-970415 (2016).
Wei et al., "Comparison of corneal sensitivity between FS-LASIK and femtosecond lenticule extraction (ReLEx flex) or small-incision lenticule extraction (ReLEx smile) for myopic eyes," Graefes Archive for Clinical and Experimental Ophthalmology, Feb. 7, 2013, vol. 251(6), pp. 1645-1654.
Wei et al., "Erratum to: Comparison of corneal sensitivity between FS-LASIK and femtosecond lenticule extraction (ReLEx flex) or small-incision lenticule extraction (ReLEx smile) for myopic eyes," Graefes Archive for Clinical and Experimental Ophthalmology, May 1, 2013, vol. 251, pp. 2495-2497.
West et al.; "Fourier Transform Infrared Spectral Analysis of Degenerative Cartilage: An Infrared Fiber Optic Probe and Imaging Study"; Applied Spectroscopy; 58(4); pp. 376-381; 2004.
Wilkinson et al.; "Refractive eye surgery: helping patients make informed decisions about LASI"; Am Fam Physician. May 15, 2017: 95(10): pp. 637-644.
Wilson SE, et al "Epithelial injury induces keratocyte apoptosis: hypothesized role for the interleukin-1 system in the modulation of corneal tissue organization and wound healing." Exp Eye Res. Apr. 1996; 62 (4): 325-7.
Wilson SE, et al "Herpes simplex virus type-1 infection of corneal epithelial cells induces apoptosis of die underlying keratocytes." Exp Eye Res. 1997;64:775-779.
Wise et al "Cytokine Expression in Keratoconus and its Corneal Microenvironment"—A Systematic Review, 2015.
Wollensak et al, "Riboflavin/ultraviolet-A-induced collagen crosslinking for the treatment of keratoconus"; Am J Ophthalmol 2003;135:620-627.
Wollensak et al., "Biomechanical Efficacy of Collagen Crosslinking in Porcine Cornea Using a Femtosecond Laser Pocket", Cornea (Mar. 1, 2014) vol. 33(3), pp. 300-305.
Wollensak G, et al. "Hydration behavior of porcine cornea cross-linked with riboflavin and ultraviolet A."; J Cataract Refract Surg. 2007;33:516-521.
Wollensak G, et al. "Interlamellar cohesion after corneal collagen crosslinking using riboflavin and ultraviolet A light.";Br J Ophthalmol. 2011;95:876-880.
Wollensak G. "Corneal collagen crosslinking: new horizons."; Expert Rev Ophthalmol. 2010;5:201-215.
Wollensak, G. et al "Biomechanical and histological changes after corneal crosslinking with and without epithelial debridement," Journal of Cataract & Refractive Surgery, 35(3), 540-546 (2009).
Wollensak, G. et al "Long-term biomechanical properties of rabbit cornea after photodynamic collagen crosslinking," Acta ophthalmologica, 87(1), 48-51 (2009).

(56) References Cited

OTHER PUBLICATIONS

Wollensak, G., "Crosslinking treatment of progressive keratoconus: new hope," Current opinion in ophthalmology, 17(4), 356-360 (2006).
Xia et al., "Low-intensity pulsed ultrasound treatment at an early osteoarthritis stage protects rabbit cartilage from damage via the integrin/focal adhesion kinase/mitogen-activated protein kinase signaling pathway," Journal of Ultrasound in Medicine, Nov. 1, 2015, vol. 34(11), pp. 1991-1999.
Xia et al.; The depth-dependent anisotropy of articular cartilage by Fourier transform infrared imaging (FTIRI); Osteoarthritis and Cartillage 15; pp. 780-788; 2007.
Zhao et al.; "Automated Autofluorescence Background Subtraction Algorithm for Biomedical Raman Spectroscopy" Applied Spectroscopy; First Published Nov. 1, 2007; vol. 61I Issue 11; pp. 1225-1232.
Zhu et al., "Corneal Crosslinking With Rose Bengal and Green Light: Efficacy and Safety Evaluation", Cornea. Sep. 2016;35(9):1234-41.
Zipfel, W.R., et al "Live tissue intrinsic emission microscopy using multi photon-excited native fluorescence and second harmonic generation," Proceedings of the National Academy of Sciences, 100(12), 7075-7080 (2003).
Albro et al.; "Synovial Fluid and Physiologic Levels of Cortisol, Insulin, and Glucose in Media Maintain the Homeostasis of Immature Bovine Cartilage Explants over Long Term Culture"; Annual Meeting of the Orthopedic Research Society; New Orleans, LA, USA; 2013.
Alexandrov; "A trust-region framework for managing the use of approximation models in optimization"; Structural Optimization 15, 16-23; Springer-Verlag; 1998.
Alió JL, et al. "Cross-linking in progressive keratoconus using an epithelial debridementor intrastromal pocket technique after previous corneal ring segment implantation." J Refract Surg. 2011; 27:737-743.
Ashkavand Z,et al "The pathophysiology of osteoarthritis" Journal of PharmacyResearch 7(1), 132-8(2013).
Asri, D.,et al "Corneal collagen crosslinking in progressive keratoconus: multicenter results from the French National Reference Center for Keratoconus," Journal of Cataract & Refractive Surgery, 37(12), 2137-2143 (2011).
Author Unknown, "New Method Could Offer More Precise Treatment for Corneal Disease", The Optical Society, May 4, 2016.
Bekesi et al., "Biomechanical Changes After In Vivo Collagen Cross-Linking With Rose Bengal-Green Light and Riboflavin-UVA", Invest Ophthalmol Vis Sci. Mar. 1, 2017;58(3):1612-1620.
Bi; "A novel method for determination of collage orientation in cartilage by Fourier transform infrared imaging spectroscopy (FT -IRIS)", Osteoarthritis and Cartilage 13; p. 1050-1058; 2005.
Bikbova G, et al "Transepithelial corneal collagen cross-linking by iontophoresis of riboflavin." Acta Ophthalmol, 2013.
Bradford et al., "Custom built nonlinear optical crosslinking (NLO CXL) device capable of producing mechanical stiffening in ex vivo rabbit corneas", Biomedical Optics Express, vol. 8 / Issue 10, pp. 4788-4797, Sep. 2017.
Caporossi A, et al. "Riboflavin-UVA-induced corneal collagen cross-linking in pediatric patients. "Cornea. 2012;31:227-231.
Chai et al., "Quantitative assessment of UVA-riboflavin corneal cross-linking using nonlinear optical microscopy," Investigative Ophthalmology & Visual Science, Jun. 1, 2011, vol. 52(7), pp. 4231-4238.
Chai, D., et al. "Nonlinear optical collagen cross-linking and mechanical stiffening: a possible photodynamic therapeutic approach to treating corneal ectasia," Journal of biomedical optics, 18(3), 038003-038003 (2013).
Chan et al., "Photochemical crosslinking improves the physicochemical properties of collagen scaffolds," Journal of Biomedical Materials Research Part A, Aug. 16, 2005, vol. 75(3), pp. 689-701.
Charles A. Dinarello, "Interleukin-1", Cytokine & Growth Factor Reviews vol. 8. No. 4, pp. 253-265, 1997.

Chen MC, et al. "Corneal biomechanical measurements before and after laser in situ keratomileusis." J Cataract Refract Surg. 2008;34:1886-1891.
Chen, S.,et al "IntraLase femtosecond laser vs mechanical microkeratomes in LASIK for myopia: a systematic review and meta-analysis," Journal of Retractive Surgery, 28(1), 15-24 (2012).
Cherfan D, Verter EE, Melki S, Gisel TE, Doyle FJ Jr, Scarcelli G, Yun SH, Redmond RW, Kochevar IE. Collagen cross-linking using rose bengal and green light to increase corneal stiffness. Invest Ophthalmol Vis Sci. May 13, 2013;54(5):3426-33.
Cherfan et al., "Collagen cross-linking using rose bengal and green light to increase corneal stiffness", Invest Ophthalmol Vis Sci. May 13, 2013;54(5):3426-33.
Chu et al.; "Early diagnosis to enable early treatment of pre-osteoarthritis"; Arthritis Research & Therapy 2012; htt;://arthritis-research.com/content/14/3/212.
Chu et al.; "Early diagnosis to enable early treatment of pre-osteoarthritis"; Arthritis Research & Therapy; Jun. 7, 2012.
Daxer A, et al. "Corneal crosslinking and visual rehabilitation in keratoconus in one session without epithelial debridement: new technique."; Cornea. 2010;29:1176-1179.
Deberg et al., "New serum biochemical markers (Coll 2-1 and Coll 2-1 NO2) for studying oxidative related type II collagen network degradation in patients with osteoarthritis and rheumatoid arthritis", Osteoarthritis and Cartilage, Mar. 2005, 13 (3), pp. 258-265.
Demirok et al., "Corneal sensation after corneal refractive surgery with small incision lenticule extraction," Optometry and Vision Science, Oct. 1, 2013, vol. 90(10), pp. 1040-1047.
Dijkgraaf et al., "Normal cartilage structure, biochemistry, and metabolism: A review of the literature" J Oral Maxillofac Surg. Oct. 1995; 53(10): pp. 924-929.
Dijkgraaf et al., "The structure, biochemistry, and metabolism of osteoarthritic cartilage: A review of the literature", J Oral Maxillofac Surg. Oct. 1995; 53(10): pp. 1182-1192.
Dong Z, et al "Collagen cross-linking with riboflavin in a femtosecond laser-created pocket in rabbit corneas: 6-month results";. Am J Ophthalmol. 2011;152:22-27.e1.
Durrie et al., "Femtosecond laser versus mechanical keratome flaps in wavefront-guided laser in situ keratomileusis: Prospective contralateral eye study", Journal of Cataract & Refractive Surgery, Jan. 1, 2005, vol. 31(1), pp. 120-126.
Esmonde-White et al., "Fiber-optic Raman Spectroscopy of Joint Tissues", Analyst. vol. 136, No. 8, Apr. 21, 2012 [retrieved on Oct. 4, 2017).
Esmonde-White,K.A., et al "Raman spectroscopy of synovial fluid as a tool for diagnosing osteoarthritis" Journal of Biomedical Optics14(3)pp. 034013 May 14, 2009.
Evans, D.F. et al "Reactivity of the (1Δg)2 and 1Δg states of oxygen produced by direct laser excitation," Journal of the Chemical Society, Faraday Transactions 2: Molecular and Chemical Physics, 72, 1661-1666 (1976).
Extended Report and Opinion issued in the corresponding EP Application No. 16858413.4, dated Aug. 30, 2018.
Eydelman M., "Symptoms and satisfaction of patients in the patient-reported outcomes with laser in situ keratomileusis (PROWL) studies", JAMA Ophthalmol Jan. 1, 2017; 135(1): pp. 13-22.
Eyre et al.; "Cross-linking in collagen and elastin"; Annual Reviews; Biochem.; 53; pp. 717-748; 1984.
Farah, S.G., et al "Laser in situ keratomileusis: literature review of a developing technique," Journal of Cataract & Refractive Surgery, 24(7), 989-1006 (1998).
Farjadnia M, et al "Corneal cross-linking treatment of keratoconus." Oman.J Ophthalmol vol. 8/ Issue 2 pp. 86-91 May 2015.
Felson et al., "Osteoarthritis: new insights. Part 1: the disease and its risk factors," Annals of Internal Medicine, Oct. 17, 2000, vol. 133(8), pp. 635-646.
Filipello M, et al "Transepithelial corneal collagen crosslinking: bilateral study." J Cataract Refract Surg. 2012;38:283-291.
Friedman et al, "Advanced corneal cross-linking system with fluorescence dosimetry"; Journal of Ophthalmology vol. 2012 Article No. 303459 Jul. 2012.

(56) References Cited

OTHER PUBLICATIONS

Gallego-Munoz et al., "Corneal Wound Repair After Rose Bengal and Green Light Crosslinking: Clinical and Histologic Study", Invest Ophthalmol Vis Sci. Jul. 1, 2017;58(9):3471-3480.
Gil et al., "Improved self-healing properties of collagen using polyurethane microcapsules containing reactive diisocyanate," Polymer International, Apr. 29, 2016, vol. 65(6), pp. 721-727.
Guo et al., "Femtosecond laser collagen cross-linking without traditional photosensitizers," Optical Interactions with Tissue and Cells XXVI, Mar. 5, 2015, vol. 9321, pp. 932103-1-932103-13.
Guo et al., "Investigation of the formation mechanism and morphology of the features created in the interior of cornea by femtosecond laser pulses," Optical Interactions with Tissue and Cells XXVI, Mar. 1, 2015, vol. 9321, pp. 932106-1-932106-14.
Hardy et al.; "The nature of the cross-linking of proteins by glutaraldehyde. Part 2. The formation of quaternary pyridinium compounds by the action of glutaraldehyde on proteins and the identification of a 3-(2-piperidyl)-pyridinium derivative, anabilysine, as a cross-linking entity"; Journal of the Chemical Soceity; Perkin Transactions; 1:2282-8 1979.
He, L., et al "Femtosecond laser-assisted cataract surgery," Current opinion in ophthalmology, 22(1), 43-52 (2011).
Helena et al. "Keratocyte apoptosis after corneal surgery," 1997.
Holden et al. "Global prevalence of myopia and high myopia and temporal trends from 2000 through 2050" Ophthalmology. May 2016;123(5): pp. 1036-1042.
Holzer MP, Rabsilber TM, Auffarth GU. Femtosecond laser-assisted corneal flap cuts: morphology, accuracy, and histopathology. Invest Ophthalmol Vis Sci. Jul. 2006;47(7):2828-31.
Hovakimyan, S.,et al "Imaging corneal crosslinking by autofluorescence 2-photon microscopy, second harmonic generation, and fluorescence lifetime measurements." Journal of Cataract & Refractive Surgery, 36(12), 2150-2159 (2010).
Hovhannisyan, V., et al "Photophysical mechanisms of collagen modification by 80 MHz femtosecond laser." Optics express 18, No. 23, 24037-24047 (2010).
International Preliminary Report on Patentability for International Application No. PCT/US2016/058353 dated May 3, 2018.
International Preliminary Report on Patentability issued in International Application No. PCT/US2017/036915 dated Dec. 20, 2018.
International Search Report and Written Opinion for International Application No. PCT/US2016/058353 dated Feb. 21, 2017.
International Search Report and Written Opinion for International Application No. PCT/US2017/036915 dated Oct. 23, 2017.
J.K.F. Tait et al.; "Fourier transform Raman spectroscopic examination of two amine-based epoxy resin crosslinking agents"; Elsevier; Spectrochimica Acta Part A 51; pp. 2101-2106; May 3, 1995.
Jastrzebska, M.,et al "Raman spectroscopic study of glutaraldehyde stabilized collagen and pericardium tissue" Journal of Biomaterials Sciencem Polymer Editionm 14 (2) pp. 185-197, Apr. 2, 2003.
Jester et al., "Non-Linear Optical Collagen Cross-Linking (NLO CXL) for Treatment of Keratoconus", Project No. 5R01EY024600-04, Jul. 31, 2019.
Jirasek et al.; "Accuracy and Precision of Manual Baseline Determination"; Applied Spectroscopy; 58012; pp. 1488-1499; 2004.
John, "A Wide-Angle View of Keratoconus," Review of Optometry, pp. 1-5, Oct. 2012.
Juhasz et al., "Time-resolved observations of shock waves and cavitation bubbles generated by femtosecond laser pulses in corneal tissue and water," Lasers in Surgery and Medicine, Jan. 1, 1996, vol. 19(1), pp. 23-31.
Juhasz, T., et al "Corneal refractive surgery with femtosecond lasers," IEEE Journal of Selected Topics in Quantum Electronics, 5(4), 902-910 (1999).
Kanellopoulos AJ, et al "Epithelial Remodeling After Femtosecond Laser-assisted High Myopic LASIK: Comparison of Stand-alone With LASIK Combined With Prophylactic High-fluence Cross-linking" Cornea vol. 33 / Issue May 5, 2014 pp. 463-469.
Kanellopoulos AJ. "Collagen cross-linking in early keratoconus with riboflavin in a femtosecond laser-created pocket: initial clinical results." J Refract Surg. 2009;25:1034-1037.
Kanellopoulos, A.J. et al "Collagen cross-linking (CCL) with sequential topography-guided PRK: a temporizing alternative for keratoconus to penetrating keratoplasty" Cornea, 26(7), 891-895 (2007).
Karamburoglu, G., et al "Intacs implantation with sequential collagen cross-linking treatment in postoperative LASIK ectasia."; J Refract Surg 2008;24:S726-S729.
Kato et al., "Topography-Guided Conductive Keratoplasty: Treatment for Advanced Keratoconus", American Journal of Ophthalmology, Oct. 1, 2010, vol. 150(4), pp. 481-489.
Kempen JH, "The prevalence of refractive errors among adults in the United States", Western Europe, and Australia. Arch. Ophthalmol. Apr. 2004; 122(4): pp. 495-505.
Kermani O, et al "Comparative micromorphologic in vitro porcine study of IntraLase and femto LDV femtosecond lasers "; J Cataract Refract Surg. 2008;34:1393-1399.
Kilic, A, et al "Riboflavin injection into the corneal channel for combined collagen crosslinking and intrastromal corneal ring segment implantation."; J Cataract Refract Surg. 2012:38:878-883.
Kling S, et al "Corneal biomechanical changes after collagen cross-linking from porcine eye inflation experiments" IOVS vol. 51/Issue 8, pp. 3961-3968, Aug. 2010.
Kolli, S. "Safety and efficacy of collagen crosslinking for the treatment of keratoconus" Expert opinion on drug safety, 9(6), 949-957 (2010).
Konig et al., "Intratissue surgery with 80 MHz nanojoule femtosecond laser pulses in the near infrared," Optics Express, Feb. 11, 2002, vol. 10(3), pp. 171-176.
Krueger RR, et al "Staged intrastromal delivery of riboflavin with UVA cross-linking in advanced bullous keratopathy: laboratory investigation and first clinical case." J Refract Surg. 2008;24:S730-S736.
Kwok et al., "Selective two-photon collagen crosslinking in situ measured by Brillouin microscopy," Optica, May 20, 2016, vol. 3(5), pp. 469-472.
Leccisotti A, et al "Transepithelial corneal collagen cross-linking in keratoconus." J Refract Surg. 2010;26:942-948.
Leger et al.; "Comparison of Derivative Preprocessing and Automated Polynomial Baseline Correction Method for Classification and Quantification of Narcotics in Solid Mixtures"; Society for Applied Spectroscopy; vol. 60; No. 2; pp. 182-193; 2006.
Leinikova et al., "Femtosecond Corneal Collagen Crosslinking in Treatment of Patients with Progressive Keratoconus Stages I-II," Clinical and Translational Medicine, 2016 (full date not available), vol. 8(1), pp. 128-132.
Lim et al.; "Epithelium-on photorefractive intrastromal cross-linking (PiXL) for reduction of low myopia"; Clin Ophthalmol. 2017; 11: pp. 1205-1211.
Liu et al. "Corneal Epithelial Wound Healing"; Progress in Molecular Biology and Translational Science, Academic Press, vol. 134, 2015, pp. 61-71.
Lombardo M, et al. "Biomechanics of the anterior human corneal tissue investigated with atomic force microscopy."; Invest Ophthalmol Vis Sci. 2012;53:1050-1057.
Lubatschowski, H., et al "Application of ultrashort laser pulses for intrastromal refractive surgery," Graefe's archive for clinical and experimental ophthalmology, 238(1), 33-39 (2000).
Marshall, J., et al "Long-term healing of the central cornea after photorefractive keratectomy using an excimer laser," Ophthalmology, 95(10), 1411-1421 (1988).
Matheson, I.B.C., et al "The quenching of singlet oxygen by amino acids and proteins," Photochemistry and photobiology, 21(3), 165-171 (1975).
Mayo et al.; "Course notes on the interpretation of infrared and Raman spectra"; John Wiley & Sons, Inc.; 2003.
Mazet et al.; "Background removal from spectra by designing and minimising a non-quadratic cost function" Chemometrics and Intelligent Laboratory Systems 76 (2005) pp. 121-133.
Medeiros FW, et al. "Biomechanical corneal changes induced by different flap thickness created by femtosecond laser."; Clinics (Sao Paulo). 2011;66:1067-1071.

(56) References Cited

OTHER PUBLICATIONS

Meier; "On art and science in curve-fitting vibrational spectra"; Vibrational Spectroscopy; vol. 39; Issue 2; pp. 266-269; Mar. 10, 2005.
Meltendorf et al., "Corneal intrastromal tissue modeling with the femtosecond laser," Graefes Archive for Clinical and Experimental Ophthalmology, Nov. 1, 2011, vol. 249(11), pp. 1661-1666.
Migneault et al.; "Glutaraldehyde: behavior in aqueous solution, reaction with proteins, and application to enzyme crosslinking"; BioTechniques 37:790-802; Nov. 2004.
Munnerlyn, C.R., et al "Photorefractive keratectomy: a technique for laser refractive surgery," Journal of Cataract & Refractive Surgery, 14(1), 46-52 (1988).
Nan Shen, "Photodisruption in biological tissues using femtosecond laser pulses." Diss. Harvard University Cambridge,Massachusetts, (2003).
Naoyuki Morishige et. al. "Quantitative Analysis of Collagen Lamellae in the Normal and Keratoconic Human Cornea by Second Harmonic Generation Imaging Microscopy," Investigative Ophthalmology & Visual Science Dec. 2014, vol. 55, 8377-8385.
Netto MV, Mohan RR, Ambrosio R Jr, Hutcheon AEK, Zieske JD, Wilson SE. Wound healing in the cornea: a review of refractive surgery complications and new prospects for therapy. Cornea Jul. 2005; 24(5): pp. 509-522.
Nguyen et al., "Corneal collagen cross-linking in the stabilization of PRK, LASIK, thermal keratoplasty, and orthokeratology," Current Opinion in Ophthalmology, Jul. 1, 2013, vol. 24(4), pp. 291-295.
Nover AB, et al "Longterm storage and preservation of tissue engineered articular cartilage." J Orthop Res. Jan. 2016;34(1):141-8.
Park, C.Y. et al "Second Harmonic Generation Imaging Analysis of Collagen Arrangement in Human Cornea" Investigative ophthalmology & visual science, 56(9), 5622-5629 (2015).
Poli M, et al. "Prospective study of corneal collagen cross-linking efficacy and tolerance in the treatment of keratoconus and corneal ectasia: 3-year results" Cornea. 2013;32:583-590.
Rabinowitz, "Keratoconus," Survey of Ophthalmology, Jan.-Feb. 1998, vol. 42(4), pp. 297-319.
Raiskup-Wolf et al., "Collagen crosslinking with riboflavin and ultraviolet-A light in keratoconus: Long-term results", Journal of Cataract & Refractive Surgery, vol. 34 (5), May 1, 2008, pp. 796-801.
Reddy et al., "Laser photostimulation of collagen production in healing rabbit achilles tendons," Lasers in Surgery and Medicine, Jan. 1, 1998, vol. 22(5), pp. 281-287.
Aristeidou et al., "The evolution of corneal and refractive surgery with the femtosecond laser", Eye Vis (Lond), Jul. 14, 2015, vol. 2(12), pp. epub.
Bakilan et al., "Effects of Native Type II Collagen Treatment on Knee Osteoarthritis: A Randomized Controlled Trial", Eurasian Journal of Medicine, vol. 48(2), pp. 95-101, Jun. 2016.
Collier et al., "Estimated burden of Keratitis—United States, 2010", MMWR Morb Mortal Wkly Rep, vol. 63(45), pp. 1027-1030, Nov. 14, 2014.
De Macedo et al., "Femtosecond laser-assisted deep anterior lamellar keratoplasty in phototherapeutic keratectomy versus the big-bubble technique in keratoconus", International Journal Ophthalmology, vol. 11(5), pp. 807-812, May 2018.
De Medeiros et al., "Effect of femtosecond laser energy level on corneal stromal cell death and inflammation", Journal of Refractive Surgery, vol. 25(10), pp. 869-874, Apr. 2009.
Deibel et al., "Ocular inflammation and infection", Emerg Med Clin North A, May 2013, vol. 21(2), pp. 387-397.
Dolgin, "Parkinson's drug makers target inflammasome", Nature Biotechnology, Jan. 2019.
Eyre, "Collagen cross-linking in skeletal aging and disease", NIH Grant# 5R37AR037318-32, Awardee: University of Washington.
Gutierrez-Bonnet et al., "Macular Choroidal Thickening in Keratoconus Patient: Swept-Source Optical Coherence Tomography Study", Translational Vision Science & Technology, vol. 7(3), p. 15, Jun. 2018.

International Search Report and Written Opinion for International Application No. PCT/US2019/015095 dated Apr. 22, 2019.
Jones et al., "Nanoscale dysregulation of collagen structure-function disrupts mechano-homeostasis and mediates pulmonary fibrosis", eLife, vol. 7, pii: e36354, Jul. 2018.
Kymionis et al., "Simultaneous topography-guided PRK followed by corneal collagen cross-linking for keratoconus", Journal of Refractory Surgery, vol. 25(9), pp. S807-822, Sep. 2009.
Legrand et al., "Glycation Marker Glucosepane Increases with the Progression of Osteoarthritis and correlates with Morphological and Functional changes of Cartilage in vivo", Arthritis Research & Therapy, vol. 20(1), p. 131, Jun. 2018.
Mittal et al., "Reactive oxygen species in inflammation and tissue injury", Antoxid Redox Signal, Oct. 2013, vol. 20(7), pp. 1126-1167.
Patel et al., "Keratocyte progenitor cell transplantation: A novel therapeutic strategy for corneal disease", Medical Hypotheses, vol. 80(2), pp. 122-124, Feb. 2013.
Price et al., "Photoactivated riboflavin treatment of infectious keratitis using collagen cross-linking technology", Journal of Refractive Surgery, vol. 28(10), pp. 706-713, Oct. 2012.
Rapuano et al., "Antimicrobial Studies Using the Therapeutic Tissue Cross-Linking Agent, Sodium Hydroxymethylglycinate: Implication for Treating Infectious Keratitis", IOVS, vol. 59(1), pp. 332-337, Jan. 2018.
Sharif et al., "Human in vitro Model Reveals the Effects of Collagen Cross-linking on Keratoconus Pathogenesis", Scientific Reports, vol. 7(1), Oct. 2017.
Shetty et al., "Collagen crosslinking in the management of advanced non-resolving microbial keratitis", Br J Opthalmol, Aug. 2014, vol. 98(8), pp. 1033-1055.
Song et al., "Viability, apoptosis, proliferation, activation, and cytokine secretion of human keratoconus keratocytes after cross-linking", Biomedical Research International, Epub 2015: 253237, Jan. 2015.
Stantchev et al., "Subwavelength hyperspectral THz Studies of Articular Cartilage", Scientific Reports, vol. 8, Published online May 2, 2018.
Tabibian et al., "PACK-CXL: Corneal Cross-linking for Treatment of Infectious Keratitis", Journal of Ophthalmic & Vision Research, vol. 10(1), pp. 77-80, Jan. 2015.
Unknown, "New noninvasive reflective treatment on the horizon", EyeWorld, Oct. 2018.
Wang et al., "Femtosecond laser crosslinking of the cornea for non-invasive vision correction", Nature Photonics, vol. 12, pp. 416-422, May 2018.
Xie et al., "Robust increase of cutaneous sensitivity, cytokine production and sympathetic sprouting in rats with localized inflammatory irritation of the spinal ganglia", Neuroscience, Nov. 2006, vol. 142(3), pp. 809-822.
Zayed et al., "Xenogenic Implantation of Equine Synovial Fluid-Derived Mesenchymal Stem Cells Leads to Articular Cartilage Regeneration", Stem Cells Int, Jun. 2018.
Zhang et al., "Cytokines, inflammation and pain", Int Anesthesiol Clin, Nov. 2009, vol. 45(2), pp. 27-37.
Clinical Trial No. NCT02208089, "Simultaneous TransPRK and Corneal Collagen Cross-Linking (TransPRKCXL)", Sponsor: Bruce Allan, Moorfields Eye Hospital NHS Foundation Trust, Aug. 4, 2014.
International Search Report and Written Opinion issued in International Application No. PCT/US2019/040728 and dated Sep. 18, 2019.
Caporossi et al., "Long-term Results of Riboflavin Ultraviolet A Corneal Collagen Cross-linking for Keratoconus in Italy: The Siena Eye Cross Study" Am J Ophthalmol. Apr. 2010; 149(4): pp. 585-593.
De Ortueta et al., "High-speed recording of thermal load during laser trans-epithelial corneal refractive surgery using a 750 Hz ablation system," Journal of Optometry, Jul. 20, 2018, vol. 12 (2), pp. 84-91.
Dorronsoro et al., "Dynamic OCT measurement of corneal deformation by an air puff in normal and cross-linked corneas", Biomedical Optics Express, vol. 3 / Issue 3, pp. 473-487, Feb. 2012.

(56) References Cited

OTHER PUBLICATIONS

International Search Report and Written Opinion dated Feb. 5, 2020 for International Patent Application No. PCT/US2019/063320.

Kanellopoulos et al., "Topography-guided Hyperopic LASIK With and Without High Irradiance Collagen Cross-linking: Initial Comparative Clinical Findings in a Contralateral Eye Study of 34 Consecutive Patients", Journal of Refractive Surgery, vol. 28 / Issue 11, pp. S837-S840, Nov. 2012.

Luz et al., "Application of corneal tomography before keratorefractive procedure for laser vision correction", Journal of Biophotonics, vol. 9 / Issue 5, pp. 445-453, Apr. 2016.

Meek et al., "Corneal cross-linking—a review", Ophthal Physiol Optics. Feb. 2013; 33(2): pp. 78-93.

Pedrigi et al., "Regional mechanical properties and stress analysis of the human anterior lens capsule", Vision Research, vol. 47 / Issue 13, pp. 1781-1789, Jun. 2007.

Rossi et al., "Modeling the load resistance in laser-assisted cornea transplantation", Proceedings of SPIE: Ophthalmic Technologies, vol. 10858, Feb. 2019.

Zaitsev et al., "Optical coherence elastography for strain dynamics measurements in laser correction of cornea shape", Journal of Biophotonics, vol. 10 / Issue 11, pp. 1450-1463, 2017.

Extended European Search Report dated Sep. 27, 2021 for European Patent Application No. 19744571.1.

Nikogosyan et al., "Two-Photon Ionization and Dissociation of Liquid Water By Powerful Laser UV Radiation", Chemical Physics 77 (1983) 131-143, pp. 131-143.

* cited by examiner

DIAGNOSIS AND TREATMENT OF COLLAGEN-CONTAINING TISSUES

CROSS-REFERENCE TO RELATED APPLICATIONS

This application claims priority to and the benefit of U.S. Provisional Patent Application No. 62/593,525 filed Dec. 1, 2017, which is hereby incorporated by reference in its entirety.

BACKGROUND

Collagen is found abundantly in various tissues, including cornea and cartilage. Treatments of cornea that increase crosslinking of collagen in the cornea may be desirable for certain conditions.

SUMMARY

According to embodiments of the disclosed subject matter, a method of altering optical characteristics of a cornea includes focusing a femtosecond laser onto a focal volume at a depth within stroma of the cornea, emitting laser pulses from the femtosecond laser at an infrared wavelength, and irradiating the stroma of the cornea by the emitted laser pulses. During the emitting, the method includes scanning a focus point of the femtosecond laser along a scanning pattern. Further, no photosensitizer is added to the cornea, the emitted laser pulses induce a low-density-plasma in the focal volume, the low-density-plasma ionizes surrounding molecules and produces reactive oxygen species, and the reactive oxygen species interact with collagen fibrils within the stroma to form crosslinks.

DETAILED DESCRIPTION

Figure 1:
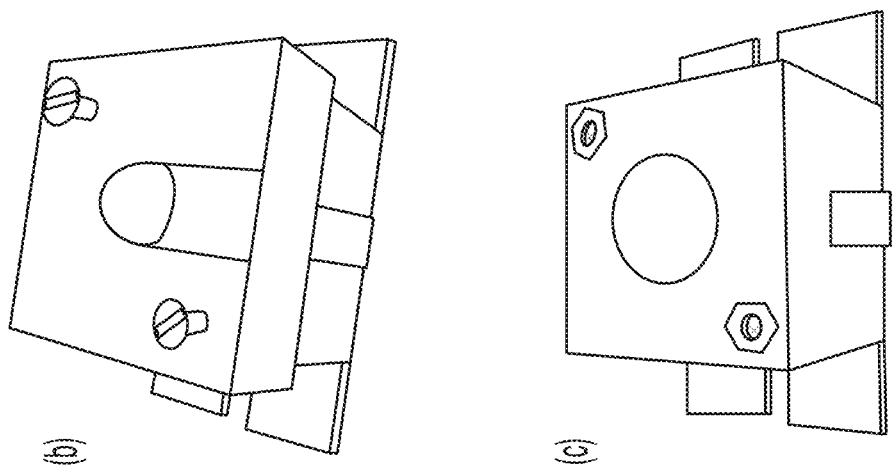
FIG. 1 (panel a) shows isolated porcine eyes in 3D printed holders connected with an IV pressure control system (panel b). (Panel c) shows a custom build eye holder.
Figure 1:
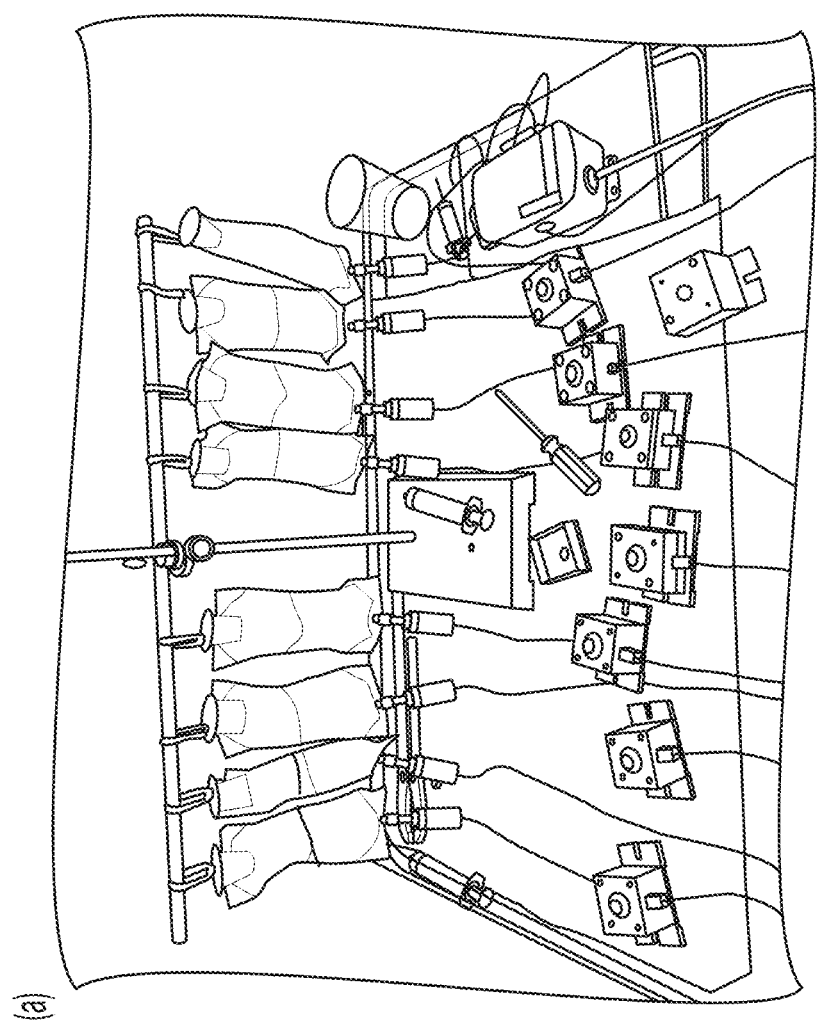

Fresh porcine eyes were obtained from an abattoir (Green Village Packing, Green Village, N.J.). Harvested eyes were transported to the laboratory on ice and treated within 3 hours after harvesting. Isolated eyes were rinsed with Dulbecco's phosphate-buffered saline (DPBS, 1×, Sigma Aldrich), inspected for presence of defects and gradually brought to a room temperature in a humidified chamber. After removing excess tissue, the eye globe was mounted onto a custom built eye holder (FIG. 1). The epithelial layer was removed from the cornea prior to the treatment. In order to maintain the eye pressure (~16 mm Hg), an intravenous (IV) system filled with the 0.9% sodium chloride solution (Hospira Inc, Lake Forest) was attached to the eyeball via 22G injection needle (BD, Franklin Lakes). A customized digital pressure gauge (Omega) was applied to adjust the pressure level (FIG. 1). Before treatment corneal surface was covered with a microscope cover glass (#1 Microscope Cover Glasses, VWR) to ensure even volumetric treatment of the cornea and reduce light scattering.

Figure 2:
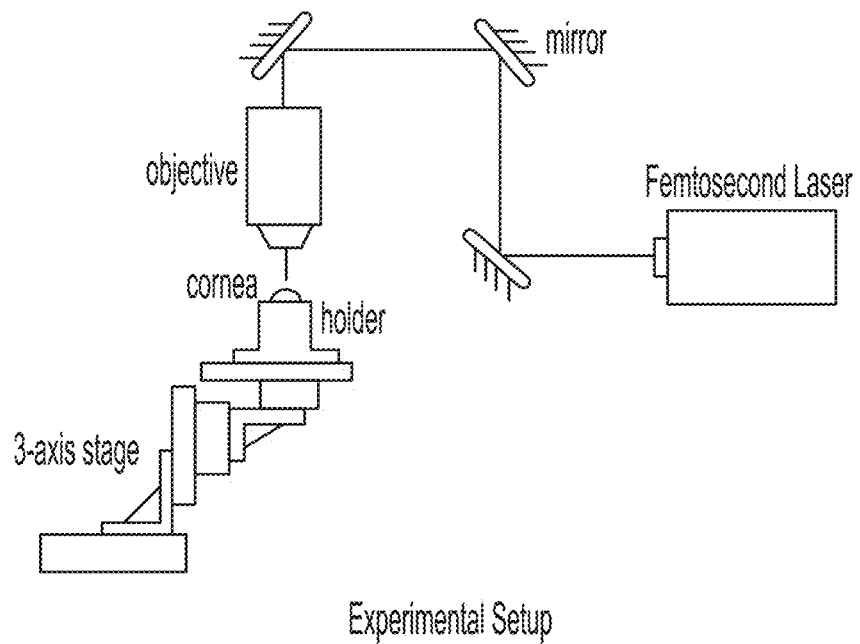
FIG. 2 shows a set up for irradiating eyes.

A Nd:Glass femtosecond laser oscillator system (High Q Laser, Spectra-Physics, Austria) was employed to generate laser pulses with temporal pulse width of 99 fs at 52.06 MHz repetition rate with central wavelength of 1060 nm. The laser was coupled with axis motorized translation stage (Thorlabs, Newton, N.J.). A Zeiss Plan-Neofluar 40x/0.6 objective lens was utilized to focus the beam, and the average power after the objective was about 60 mW. Schematic diagram depicting the experimental setup is shown in FIG. 2.

Figure 3:
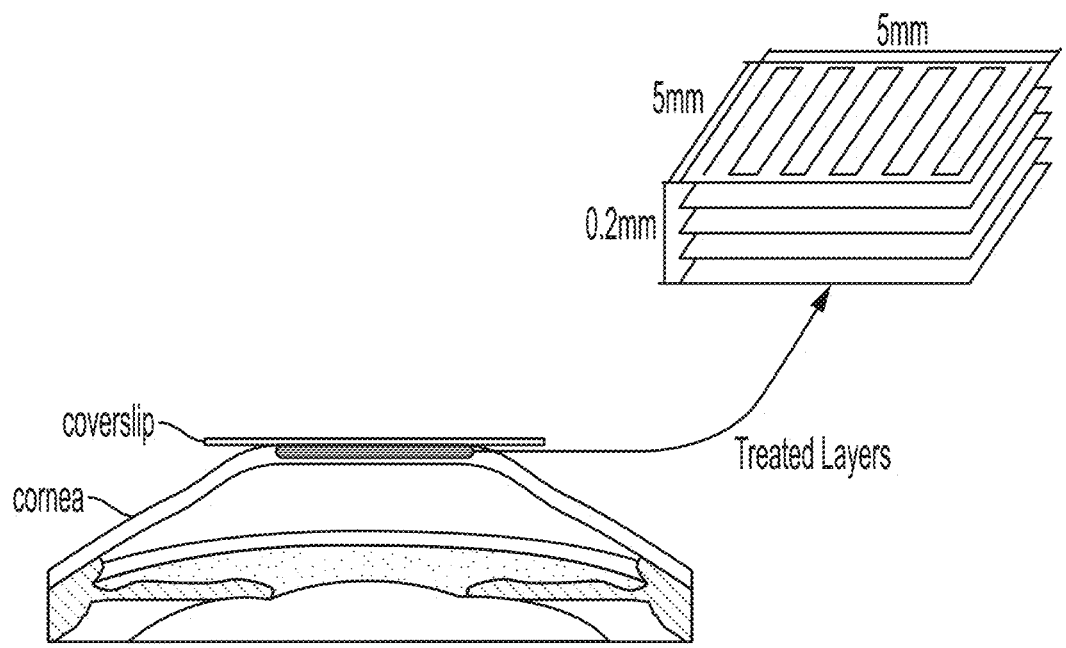
FIG. 3 shows a laser treatment pattern: five mutually independent layers were treated with 50 μm in between two layers and each layer was treated through a zigzag path.

The laser beam was initially focused on the superficial surface of the cornea. Laser pulses were delivered within a 25 mm2 square in the central zone via zig-zag motion of the focused beam at 1 mm/s feedrate. Multiple planes parallel to the corneal surface were treated with 50 μm distance between two consecutive planes. Schematic diagrams of treatment paths are shown in FIG. 3. A paired control eye was placed on the same stage for every treatment. After the treatment the cover glass was carefully removed and corneal tissue was isolated form eye globe, and prepared for second harmonic generation (SHG) and two photon autofluorescence (TPF) imaging.

FIG. 3 shows a laser treatment pattern: five mutually independent layers were treated with 50 μm in between two layers and each layer was treated through a zigzag path.

Two Photon Fluorescence (TPF) microscopy. Immediately after the treatment corneal samples were sliced into 2 mm2 blocks with a custom built slicer and mounted by 50% glycerol in PBS in a 3 mm Petri dish. The Petri dish was then filled with PBS solution for TPF imaging. Experiments were conducted using a two-photon microscope (Bruker, Mass., USA), which utilizes Mai Tai Deep See Ti:Sapphire laser (Spectra Physics, Santa Clara, Calif., USA) as the excitation source. A 40x/0.8 NA water immersion objective (Olympus, Japan) was used to collect the fluorescence signal. The signal was registered with two different photomultiplier tubes, one in the red (580-620 nm) and one in the green (480-570 nm) wavelength regime. Excitation wavelengths wavelengths used were 826 nm and 710 nm to excite collagen matrix and cellular structure, respectively.

Figure 4:
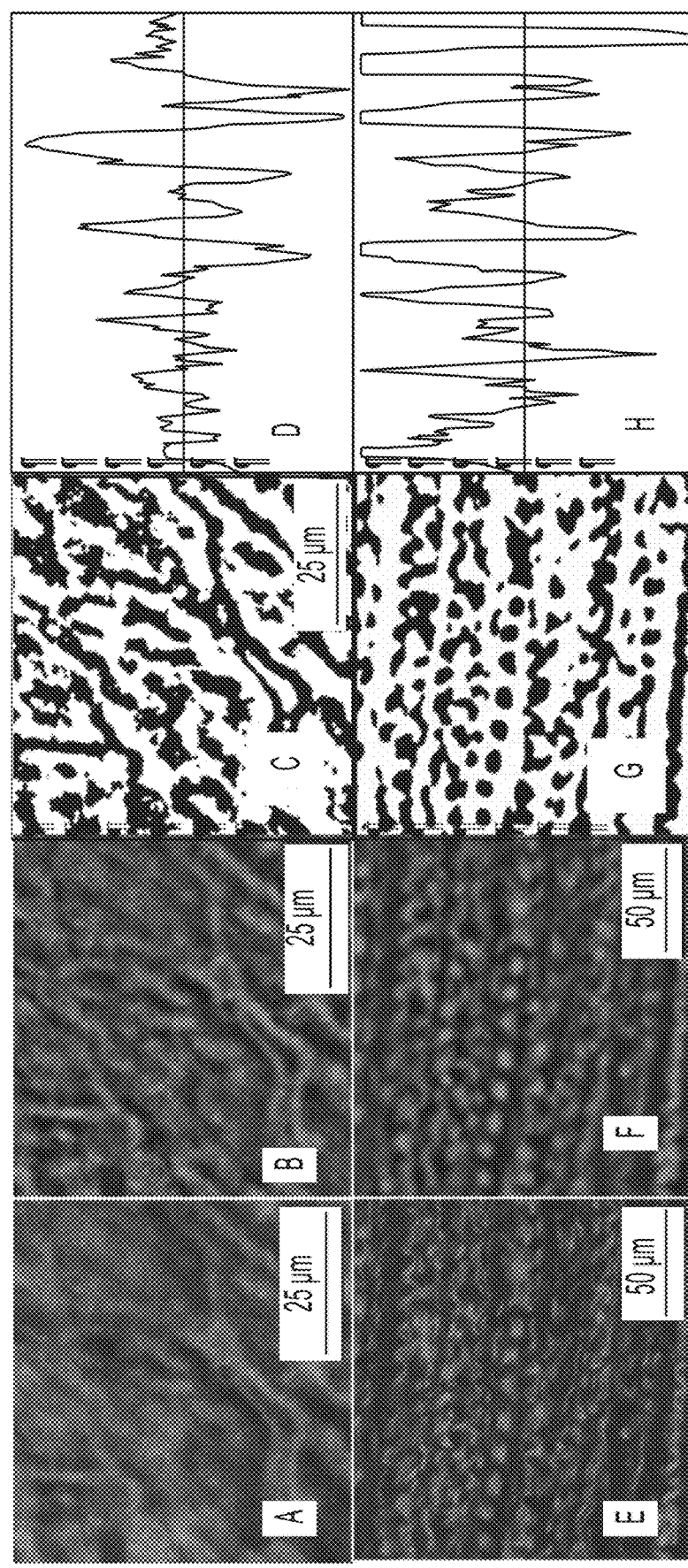
FIG. 4. shows processing of SHG images of lateral (A-D) and sagittal (E-H) sections of porcine cornea. A E—original SHG images; B, F—the same A and E images processed by application of spatial frequency filters; C, G—the filtered image B and F converted to binary; These final images were used to analyze the complexity of collagen bundle arrangement. D, H— the black and white conversions along the vertical lines in C and G are plotted as peaks in the graphs.

Second Harmonic Generation (SHG) microscopy. Corneas were harvested from treated eyes immediately after the laser irradiation and fixed overnight in 4% paraformaldehyde. Corneal blocks with 2 mm2 cross-sectional area were dissected from the central and peripheral regions after the fixation, washed with PBS, mounted on microscope cover glass with 50% glycerol in PBS and imaged. Detailed description of the characterization process can be found in Morishige et al. Second harmonic generation signal was generated by a pulsed laser (Chameleon Vision II, Coherent, Santa Clara, Calif.) tuned to 850 nm, on a A1RMP laser scanning system mounted on an Eclipse TiE microscope stand (Nikon Instruments, Melville, N.Y.) equipped with a 25x/1.1 NA ApoLWD water-immersion objective. The SHG signal was collected in the back-scattered configuration using a non-descanned detector (Nikon, Japan) with a 400-450 nm bandpass filter. The microscope was controlled using NIS Elements software (Nikon, Japan). Collected SHG images were processed by sequential application of image modifications. Briefly, an image was processed by application the bandpass filter with 100 and 20 pixels setup for large and small structures respectively. The images were filtered and then converted to binary signal, and plotted. The optical density of black and white areas in converted images was measured as the number of peaks crossing median cut-off intensity (FIG. 4). The measured crossing densities at vertical midline are considered to represent the complexity (irregularity) of collagen structure patterns. Higher the crossing density, the more complex the pattern is. We compared the crossing density along differing depths (anterior, middle, and posterior) and different regions (central and peripheral zones) of cornea. A total of 6 corneas were used and three groups of samples were prepared for SHG imaging for this study.

Figure 5:
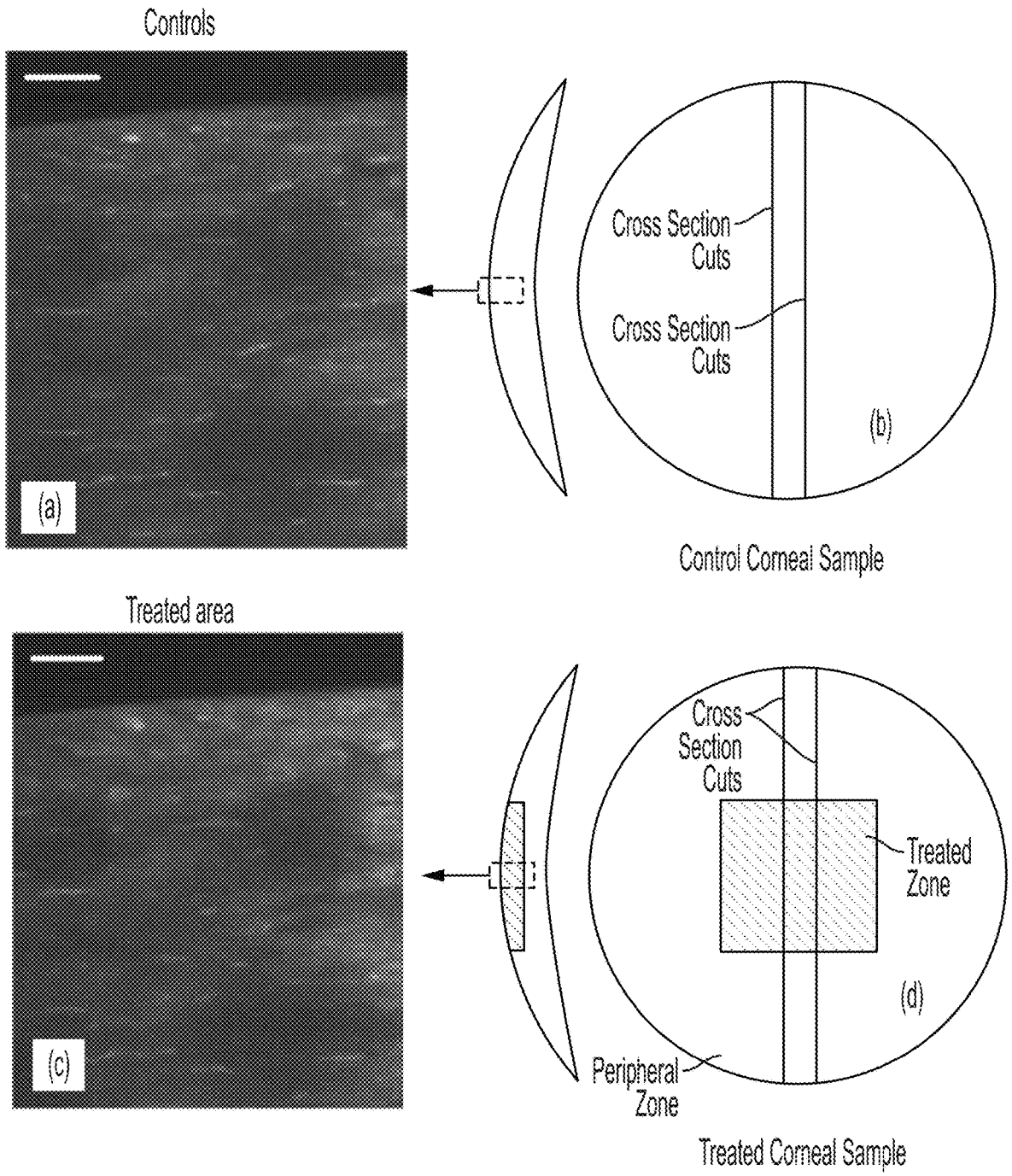
FIG. 5(b) shows an imaging region of a control sample and (d) shows the imaging region of ultrafast laser treated eyes. TPF microscopy of cross-section cuts under the excitation wavelength 710 nm (excitation for cellular structure) of (a) control and (d) laser treated corneal samples. The recorded cytoplasmic signal is based on NAD(P)H in mitochondria. The cellular structure excitation for both control and laser treated cornea samples shows a dense keratocyte network and thus no cell damage during the treatment. White color scale bar shown in FIGS. 5A and 5C is 60 μm.

Group 1 comprises the blocks dissected from the central corneal zone of the laser treated and untreated, control eyes for visualization of collagen structures in the lateral, parallel to the surface sections of the cornea. Group 2 comprises corneal blocks dissected from the central, treated and peripheral, untreated zones of the same cornea for visualization of collagen structures in lateral sections. Group 3 comprises the blocks dissected from the central corneal zones of untreated, control eyes for visualization of the sagittal sections, perpendicular to the cornea sections In the concurrent study (See Sections A and B below) we have demonstrated that the proposed treatment successfully adjusts the effective refractive power of the eye. Depending on the shape of the treated volumetric region, one can flatten the cornea to correct nearsightedness, or steepen it to address refractive errors related to hyperopia (results shown in Sections A and B). To address one safety aspect of the treatment, two photon fluorescence imaging was employed to investigate potential changes in cellular structure within the corneal tissue after the laser treatment. Since it is known that UVA light/riboflavin treatment damages keratocytes, it was of interest to determine whether NIR treatment may have adverse effect onto the cells present in the corneal stroma. 710 nm excitation length was chosen because the primary intracellular sources of fluorescence are flavins, retinol, NAD(P)H, as well as tryptophan and its indoleamine derivatives. For intrinsic autofluorophores the two-photon excitation cross-sections have their maxima in 700-750 nm range, hence the chosen excitation wavelength was 710 nm. FIG. 5 shows TPF image of the control (FIG. 5a) and treated (FIG. 5b) cornea cross-sections. The keratocyte network is relatively uniform and similar in both, control and treated corneas, with both images being in agreement with previous studies. This finding implies that NIR laser treatment does not damage cell population via induction of cell apoptosis. This is in sharp contrast with results reported by Steven et al. in which TPF images of UVA/riboflavin treated corneas have homogeneous autofluorescence signal and notable absence of keratocyte network.

FIG. 5, Imaging regions of (c) control and (d) ultrafast laser treated eyes. TPF microscopy of cross-section cuts under the excitation wavelength 710 nm (excitation for cellular structure) of (c) control and (d) laser treated corneal samples. The recorded cytoplasmic signal is based on NAD (P)H in mitochndria. The cellular structure excitation for both control and laser treated cornea samples shows a dense keratocyte network and thus no cell damage during the treatment. Scale bar: 60 μm.

Figure 6:
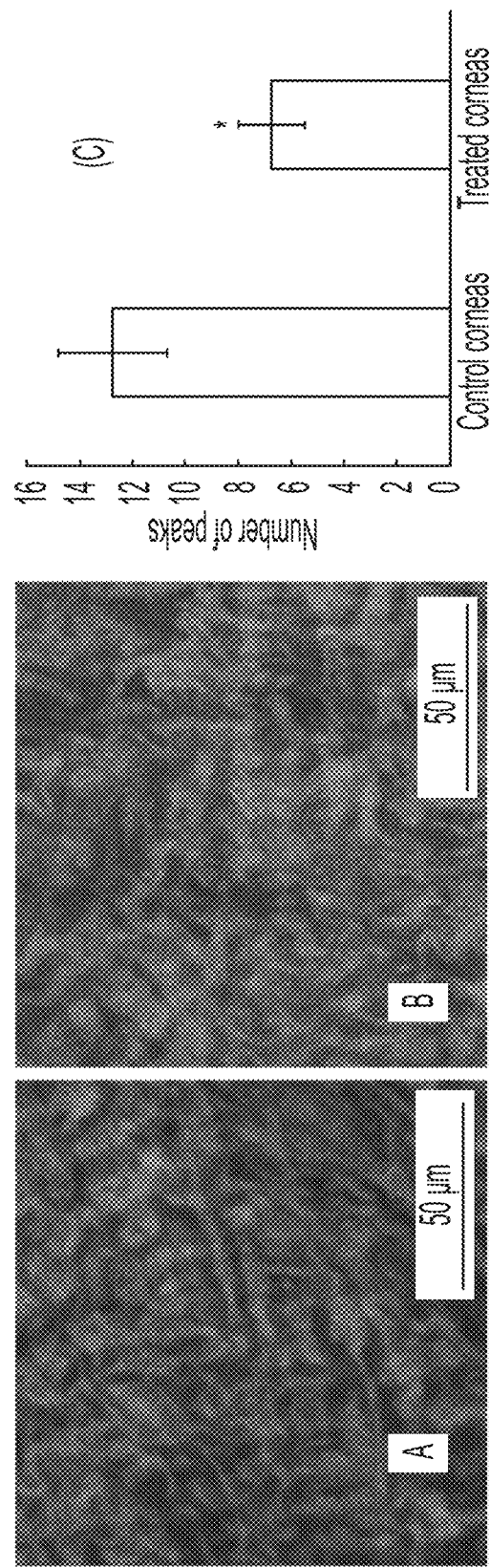
FIG. 6 shows SHG images of anterior stroma of the control (A) and the laser treated (B) porcine eyes. (C) The number of peaks counted over the cut off line on the plots of the control and laser treated corneal images (n–3). *p<0.05: statistical change from control corneas value.

The second harmonic generation (SHG) imaging microscopy was used to visualize and compare collagen structures in lateral and sagittal sections of intact and treated with near-IR femtosecond laser irradiation porcine corneas. SHG images of the collected corneal samples show the wavelike pattern of the anterior stroma of the untreated, control samples, which is consistent with prior reports. Images obtained from the harvested corneas of laser treated eyes show more solid, uniform collagen structure of the anterior stroma when compared against the control samples, (FIG. 6, A and B). The number of peaks crossing the median cut-off value of signal intensity was counted and used to quantify the irregularity of collagen arrangement patterns. Quantitative analysis of the irregularity of the collagen bundle layout on the surface of the laser treated and control corneas shows that mean irregularity of the collagen bundle patterns of the treated corneas was significantly lower when compared against to controls (FIG. 6, C).

FIG. 6 shows SHG images of anterior stroma of the control (A) and the laser treated (B) porcine eyes. (C) The number of peaks counted over the cut off line on the plots of the control and laser treated corneal images (n–3). *$p<0.05$: statistical change from control corneas value.

Figure 7:
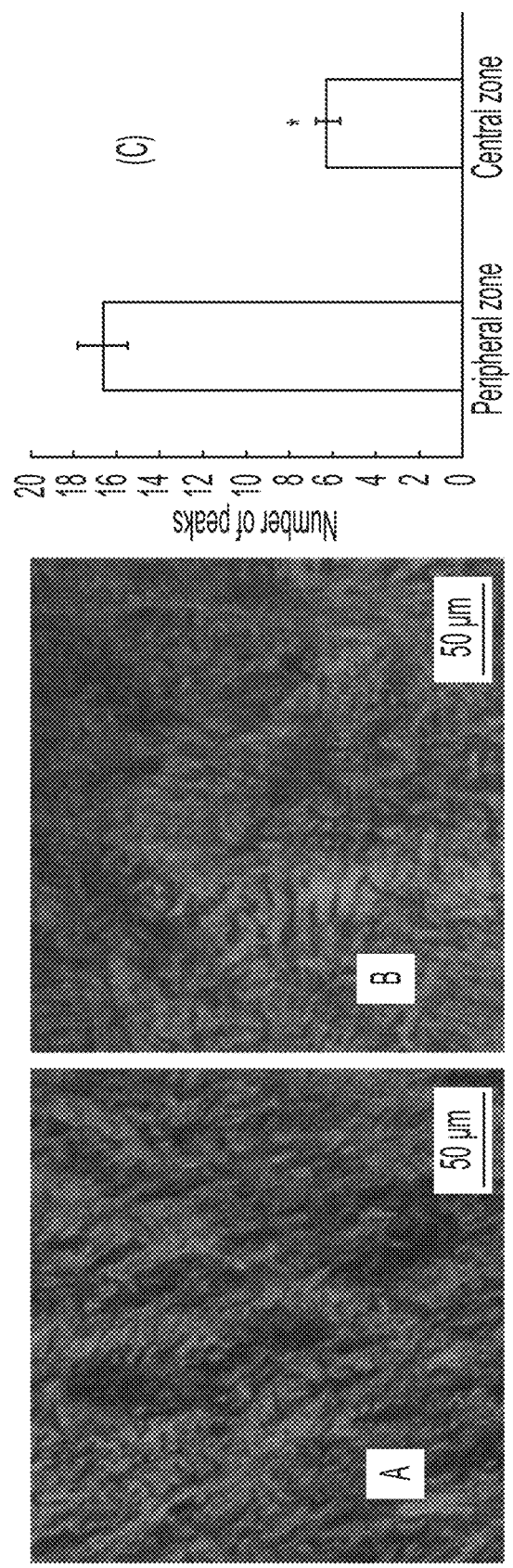
FIG. 7 SHG images of anterior stroma samples collected from peripheral (A) and central (B) zones of the laser treated corneas. (C) The number of peaks counted over the cut off line on the plots of the SHG images of the central and peripheral zones of the laser treated corneas (n=3). *p<0.05: statistical change from peripheral zone value.

The irregularity of the horizontal collagen structure layout on the anterior stroma of the laser treated corneas is markedly higher in peripheral than in central corneal zones. SHG signal collected from the central region of the treated corneas shows more uniform, homogenous collagen structures of the anterior stroma when compared against the peripheral zone (FIG. 7, A and B). The quantitative image analysis also demonstrates the lower number of the peaks crossing the median cut-off value of signal intensity for the collagen bundle patterns for central than for peripheral zone of the laser treated corneas (FIG. 7, C).

FIG. 7 SHG images of anterior stroma samples collected from peripheral (A) and central (B) zones of the laser treated corneas. (C) The number of peaks counted over the cut off line on the plots of the SHG images of the central and peripheral zones of the laser treated corneas (n=3). *$p<0.05$: statistical change from peripheral zone value.

Figure 8:
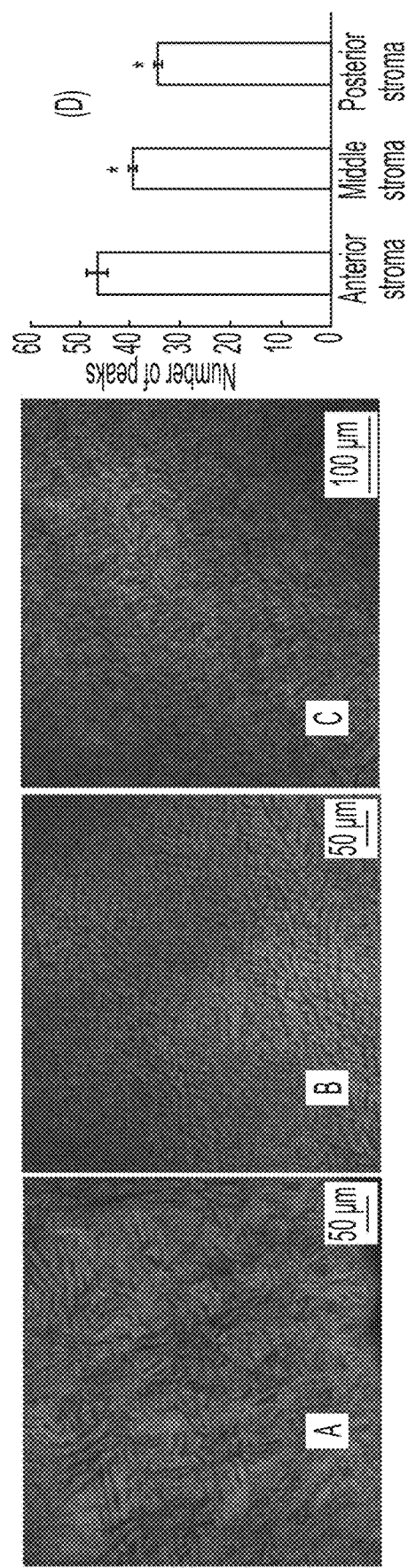
FIG. 8. SHG images of the anterior (A), middle (B) and posterior (C) layers of the control, untreated corneal stroma. (D) The number of peaks counted over the cut off line on the plots of the anterior, middle and posterior layers of the control, untreated corneas (n=3). *p<0.5: statistical change from anterior stroma value.

FIG. 8 represents a set of SHG images of the lateral sections of the control corneal stroma collected at different axial depths. The anterior layer shows the most irregular, wavelike pattern of the collagen structures. At the same conditions the middle and the posterior layers appear more homogenous. The quantitative analysis confirms the differences in the irregularity of horizontal arrangement of the collagen at different axial depths of corneas. The crossing density decries from the anterior through the middle toward posterior stroma of the control corneas (FIG. 8, D).

FIG. 8. SHG images of the anterior (A), middle (B) and posterior (C) layers of the control, untreated corneal stroma. (D) The number of peaks counted over the cut off line on the plots of the anterior, middle and posterior layers of the control, untreated corneas (n=3). *$p<0.5$: statistical change from anterior stroma value.

Figure 9:
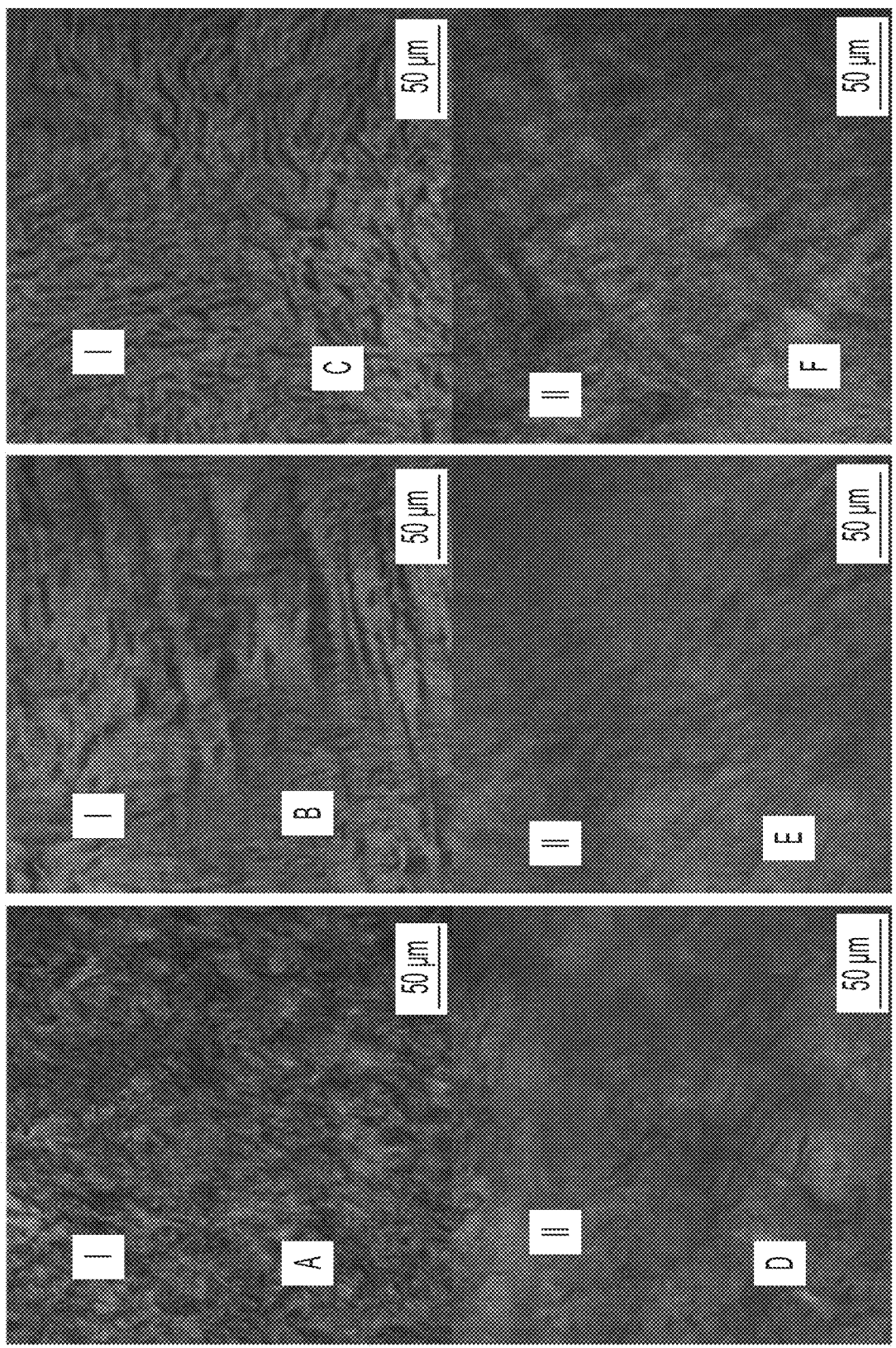
FIG. 9. SHG images of the anterior (A,D), middle (B,E) and posterior (C,F) layers of the peripheral (I) and central (II) zones of the laser treated corneas. (G) The number of peaks counted over the cut off line on the plots of the anterior, middle and posterior layers of the central and peripheral zones of the laser treated corneas (n=3).
Figure 9:
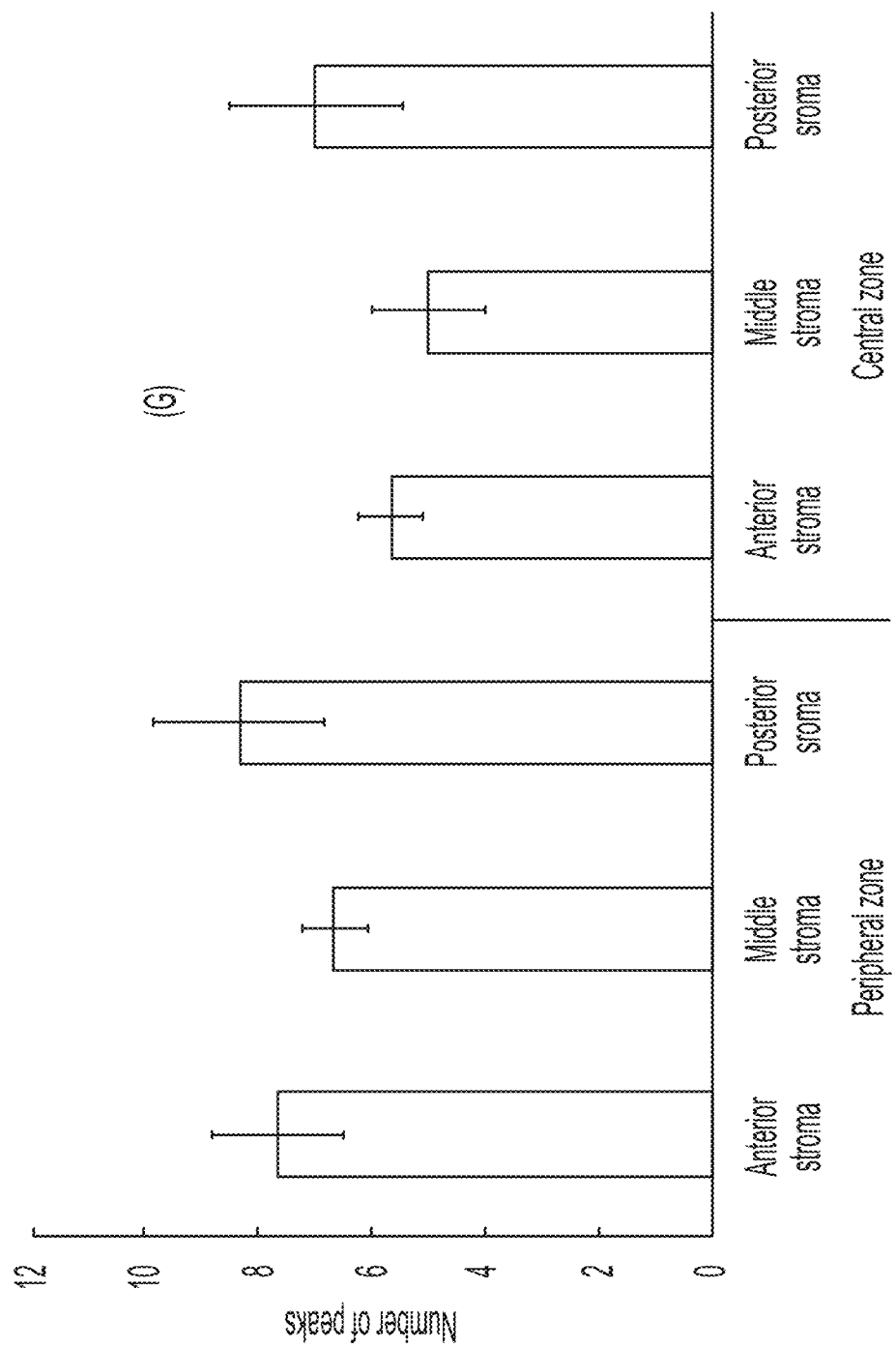

Interestingly, SHG signal of collagen structures collected from the central and peripheral zones of the treated corneas also shows changes in the pattern appearances when moving from the anterior toward posterior stroma (FIG. 9). However, the quantitative analysis of the SHG images of the samples reviled no significant changes in the in the irregularity of horizontal arrangement of the collagen bundle patterns at the different axial depths in the central and peripheral zones of the laser treated corneas. Tough the treated cornea also shows higher level of the pattern irregularity in the peripheral zone than in the central zone (FIG. 9, G).

FIG. 9. SHG images of the anterior (A,D), middle (B,E) and posterior (C,D) layers of the peripheral (I) and central (II) zones of the laser treated corneas. (G) The number of peaks counted over the cut off line on the plots of the anterior, middle and posterior layers of the central and peripheral zones of the laser treated corneas (n=3).

The ability to detect SHG signals from the cornea was first demonstrated by Hochheimer using a pulsed YAG laser. From that time Second Harmonic Generation microscopy was developed as an effective tool for direct visualization of collagen assemblies particularly of fibrillar type I collagen fibers—the structures mainly responsible for biomechanical behavior of the cornea.

In our study we characterized structural changes of porcine cornea treated with the femtosecond laser irradiation using SHG-imaging of lateral sections of the stroma at different axial depths. Though the individual collagen fibrils are not distinguishable in the images of the signal collected in back-scattered arrangement, specific collagen bundle arrangements and structural alterations are visible in SHG. The results show the wavelike pattern for anterior stroma of the intact untreated corneas. Moving from the anterior toward the posterior layers the images appear more solid, homogenous in the set of the untreated, control samples. The results are consistent with Chou Yung Park et al, generated with their serial high-resolution lamellar SHG images of the human cornea at different axial depth. The quantitative analysis of the collected SHG signals, performed as measuring of optical density of black and white areas in the converted to binary and plotted images, confirms that the irregularity in the horizontal arrangement of the collagen bundles is higher at anterior layer of the untreated cornea and decrease toward posterior layers.

The SHG imaging and subsequent quantitative analysis of the treated cornea samples reveal capability of the femtosecond laser irradiation to alter structural arrangement of the stromal collagen matrix. SGH signal collected from the anterior layers of the treated corneas shows more homogenies, with lower irregularity patterns of the collagen bundles comparing to the untreated samples. Treatment depth is approximately 250 μm when measured from of the top of the anterior stroma. SHG imaging of lateral sections at different axial depth, of the treated corneas expectedly demonstrates the highest alteration effect of the femtosecond laser irradiation in the anterior stroma. The quantitative analysis shows that as lower discrepancy in measured irregularity between anterior and middle layers of the treated samples when compared to the untreated control.

The cornea with its main function of transmitting and focusing light on the retina, provides about 80% of the refractive power of the eye. The optical performance of the cornea greatly depends on the ocular pressure and mechanical properties of the stroma. Small changes in their balance may affect the vision. Spatially resolved alteration of the mechanical properties through laser-assisted increase of crosslink density, results in the correction of the overall corneal curvature and thus change of the refractive power of the eye. This is achieved by targeting microstructural arrangement of the extracellular collagen matrix of the corneal stroma. Presented work, together with the results from our concurrent study, provide evidence that the laser-induced crosslinks are responsible for the microstructural rearrangement of the stromal collagen matrix The treatment induces a low density plasma that ionizes and dissociates water content within the focal volume and the produced ROS interacts with proteins in the collagen matrix to form crosslinks. This results in the densification of the stromal lamellae, which consequentially reduces its thickness. Cumulatively, the lamellar densification may be one of major mechanisms leading to the modifications in the overall shape of the corneal curvature and therefore change in the eye refractive power. The proposed method is particularly appealing as it does not require use of photosensitizer or any other aids, and utilizes extremely low laser pulse energies. Further the underlying ionization and dissociation mechanism is wavelength independent, which enables use of NIR frequencies which have less adverse effects to the keratocytes than UVA light. Finally, the presence of newly formed crosslinks stabilizes the cornea which can be appealing for treatment of corneal ectasia.

Femtosecond Laser Irradiation as Novel Paradigm for Treatment of Early Osteoarthritis Methods: Cartilage explants (Ø5 mm×1.6 mm and Ø5 mm×3.0 mm, thickness realized by a 3D printed slicer) were harvested from three immature bovine proximal tibias with their articular surfaces intact. The treatment was performed with a Nd:Glass High-Q Femtosecond laser oscillator system (temporal pulse width of 99 fs and 52.06 MHz repetition rate) coupled with a 3-axis translational stage (Thorlabs, Inc.). The output wavelength was centered around 1060 nm, and the high numerical aperture objective (Zeiss, Plan Neofluar 40x/0.6) delivered about 60 mW at the focal point. Treatment consisted of applying laser pulses by moving the stage in a x-y plane such that the laser path followed a zigzag pattern at a feed rate of 2.2 mm/s, thus treating a planar surface at the specific depth. The treatment was repeated at different depths, effectively inducing 'treatment layers'. Multiple treatment layers parallel to the superficial surface were applied with 50 μm distance between two consecutive planes. The specimens were gently inserted in a custom made holder with Ø5 mm holes and kept moisturized during the treatment in a PBS bath. Two batches of experiments were carried out in this study, with each batch executed on a different joint. In the first batch, six specimens were treated with the femtosecond laser, each requiring 1 hr, and was paired with an untreated control specimen that was placed next to the treated sample in the identical holder. All conditions except the laser treatment were the same for the paired controls and treated samples during the test. Two additional samples were used as fresh controls. In the second batch, five controls and five treated samples were used. Three of the treated samples received five laser treated layers. The remaining two specimens were exposed to ten laser treated layers. Cartilage explants were tested in a custom device under unconfined compression, using a creep tare load (0.1 N, 400 s) followed by stress-relaxation to 10% strain (0.5 μm/s ramp, 1800 s). The equilibrium Young's modulus (Ey) was calculated from the explant cross-sectional area, the equilibrium load and the displacement. One-way ANOVA analysis was performed to analyze data.

Results: In the first batch of experiments, laser treated samples were stiffened about 21% in comparison to the controls ($p<0.003$). Both paired and fresh controls had similar Young's modulus (FIG. 1a). The second batch of experiments has shown similar stiffening of the specimens treated with five layers in comparison to the controls ($p<0.05$). However the samples treated with ten layers showed a significant decrease in Ey ($p<0.001$, FIG. 1b).

Discussion: Collagen (COL) is the major structural protein of most connective tissues. The structural integrity and mechanical properties of articular cartilage are significantly affected by collagen cross-links, chemical compounds that connect COL fibrils as well as molecules within the collagen. When a femtosecond oscillator operates in a regime below the optical breakdown threshold, a low density plasma is created within the focal volume. This plasma is not sufficiently energetic to produce a shock wave, and thus the interaction between the laser and the affected tissue is photochemical, which leads to ionization of the matter within the focal volume and in its vicinity. Radicals produced by the ionization field interact with the COL fibrils, which in turn produce CxLs. Therefore, it appears that laser induced CxLs are responsible for stiffening of the cartilage, which in turn yields enhancement of mechanical properties (FIG. 1a and FIG. 1b). Free radicals created by the multiphoton ionization may be responsible for COL CxLs within articular cartilage. Our recent experiments have shown that ultrafast irradiation with infrared (IR) laser pulses ionize water molecules in the target tissue similar to. However, the interaction mechanism is multiphoton, rather than two-photon ionization. This is significant as it allows treatment with IR rather than ultraviolet (UV) pulses and much lower pulse energies. Ionization of the water content within the focal volume in the interior of the articular cartilage yields hydroxyl radicals, OH*, hydrogen ions $H3O^+$, and likely singlet oxygen among other species. Free radicals interact with the COL matrix producing CxLs. These newly formed CxLs are different from the ones that naturally occur in ECM, such as hydroxylysylpyridinoline. One of the CxLs formed is likely 1,3-dityrosine. However, results of the ten-layer treated samples suggest that the structure of the cartilage may be broken with excessive treatment (FIG. 1b). This interesting outcome reflects the complexity of the ultrafast laser-tissue interaction at low-density plasma regime and will be the subject of a subsequent study.

FIG. 10(a) Mechanical property characterization of laser treated samples, paired controls and fresh controls. (b) Mechanical property test of controls, five layers treated samples and ten layers treated samples. *$p<0.05$: statistical change from corresponding initial value.

Quantitative Raman Characterization of Cross-Linked Collagen Thin Films as a Model System for Diagnosing Early Osteoarthritis The onset of osteoarthritis (OA) in articular cartilage is characterized by degradation of extracellular matrix (ECM). Specifically, breakage of cross-links between collagen fibrils in the articular cartilage leads to loss of structural integrity of the bulk tissue. Since there are no broadly accepted, non-invasive, label-free tools for diagnosing OA at its early stage, Raman spectroscopy is therefore proposed in this work as a novel, non-destructive diagnostic tool. In this study, collagen thin films were employed to act as a simplified model system of the cartilage collagen extracellular matrix. Cross-link formation was controlled via exposure to glutaraldehyde (GA), by varying exposure time and concentration levels, and Raman spectral information was collected to quantitatively characterize the cross-link assignments imparted to the collagen thin films during treatment. A novel, quantitative method was developed to analyze the Raman signal obtained from collagen thin films. Segments of Raman signal were decomposed and modeled as the sum of individual bands, providing an optimization function for subsequent curve fitting against experimental findings. Relative changes in the concentration of the GA-induced pyridinium cross-links were extracted from the model, as a function of the exposure to GA. Spatially resolved characterization enabled construction of spectral maps of the collagen thin films, which provided detailed information about the variation of cross-link formation at various locations on the specimen. Results showed that Raman spectral data correlate with glutaraldehyde treatment and therefore may be used as a proxy by which to measure loss of collagen cross-links in vivo. This study proposes a promising system of identifying onset of OA and may enable early intervention treatments that may serve to slow or prevent osteoarthritis progression.

In this study, COL thin films are employed as a simplified model of collagenous extracellular matrix found in articular cartilage. Raman spectroscopy is utilized to assess changes of the relative concentration of CxLs induced by glutaraldehyde fixation. To achieve this goal, a quantitative method is developed whereby the relatively complex Raman signal obtained from the collagen is decomposed into known chemical structures and their allowable vibrational modes. Each of the structures is then modeled as a mathematical function and their sum forms an optimization function that produces model of the spectra via curve fitting. Relevant information on the CxLs is then extracted from the model. Quantitatively assessing relative CxL concentrations in articular cartilage is proposed as an avenue for diagnosing early OA.

Figure 10:
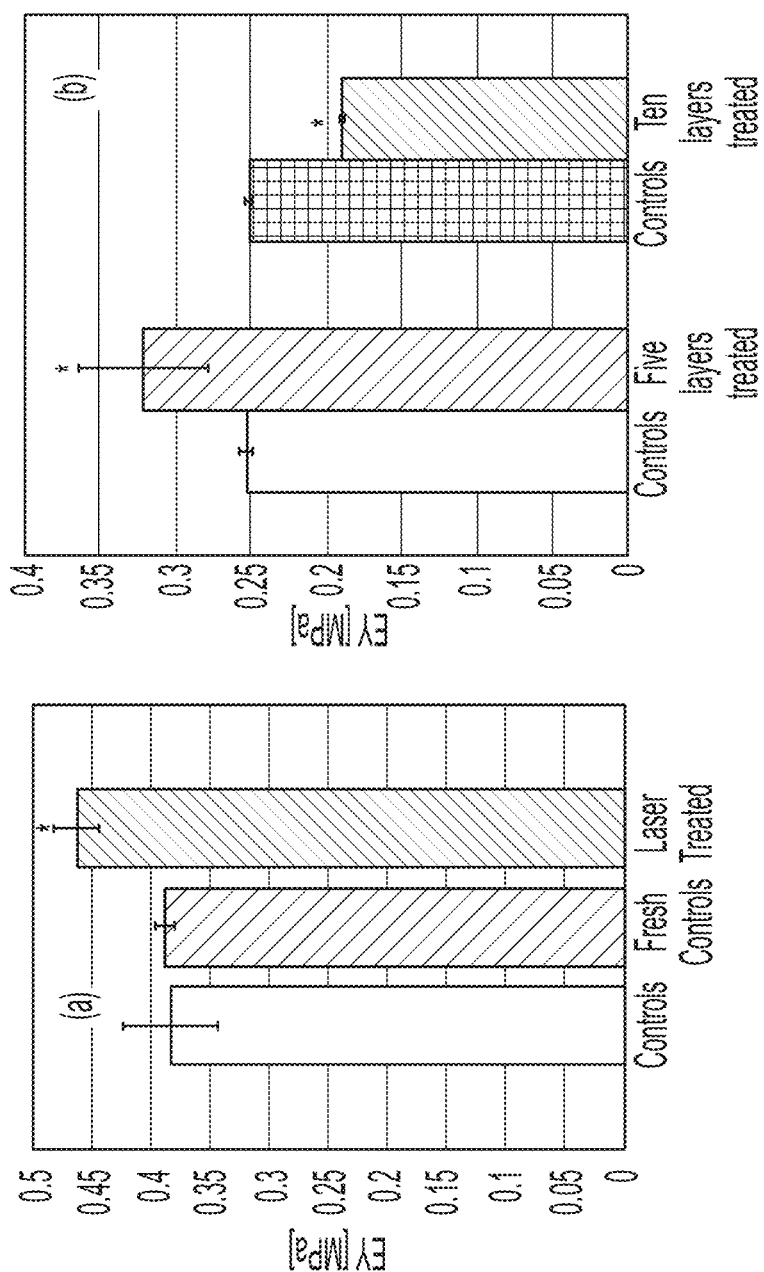
FIG. 10(*a*) Mechanical property characterization of laser treated samples, paired controls and fresh controls. (b) Mechanical property test of controls, five layers treated samples and ten layers treated samples. *p<0.05: statistical change from corresponding initial value.

Neutralized collagen solution (PH 7.4) was prepared from 3.1 mg/ml type I collagen from bovine hides (PureCol, Advanced Biomatrix San Diego, Calif., USA) in 10× Dulbecco's phosphate buffered saline (DPBS) and 0.1M NaOH. Neutralized COL solutions were applied on alkanethiol treated gold-coated silicon wafers to produce thin films. Before being used to prepare thin films, the substrates were cut into 15 mm×15 mm pieces and placed in petri dishes. Silicon substrates were coated with a 5 nm layer of chromium and 18 nm layer of gold through thermal deposition (Edwards BOC/Auto 306 Thermal Evaporator) and rinsed with ethanol. Coating was introduced to reduce fluorescence background to the Raman spectra. 1.8 ml of the neutralized COL solution was applied onto a coated silicon wafer in a petri dish and then incubated at 37° C. for 12 h. After incubation, the samples were immersed in 1-hexadecanethiol (0.5 mM; Sigma Aldrich) ethanol solution for 8 h prior to being rinsed with ethanol and dried with filtered N2. Incubated collagen was rinsed with 1× DPBS and deionized H2O 10 times to remove the bulk salt and gels from the surface. After rinsing, specimens were immediately placed in DPBS (1×) and stored at 4° C. Prior to treatment/characterization, samples were taken out of the DPBS, rinsed with deionized H2O and dried with a filtered nitrogen gun. The degree of fiber polymerization of thin films was assessed via atomic force microscopy (PSIA XE-100 AFM (Park Systems, Santa Clara, Calif., USA), whereas thickness and surface uniformity were characterized with optical profilometer (FIG. 10).

Glutaraldehyde (GA) solution, being a known cross-linker, has been used to introduce various levels of collagen cross-links. Varying exposure and concentration of GA solution controlled CxL concentration levels. Three batches of samples were treated with GA concentrations of 0.05%, 0.1% and 0.2%, respectively. There were seven samples within each batch, fixation times were 1 h, 1.5 h, 2 h, 2.5 h, 3 h and 4 h. 5 ml of GA solution was applied onto each sample. After the fixation cross-linked COL films were rinsed with deionized water and desorbed into 20 ml PBS (0.2 M, PH 7.4, Sigma Aldrich) for 48-72 h. Subsequently, specimens were rinsed with deionized H2O and DPBS (1×) several times, stored in DPBS(1×) at 4° C. and kept sterile. Cross-linked COL thin films were rinsed with deionized H2O prior to Raman characterization.

Raman spectra were acquired with a confocal microspectrometer (InVia, Renishaw Wotton-under-Edge, Gloucestershire, UK). Incident laser excitation was provided by helium-neon laser with 632.8 nm wavelength, delivered by 100× objective. Spectral resolution provided by 1800 gr/mm diffraction grating was 1 $cm^{-1}$. Raman signal was acquired with 10 accumulations, each lasting 10 s. Prior to the acquisition of the spectrum at each measurement point, photobleaching was applied for 10 s to reduce the fluorescence background. Spatially resolved characterization was performed to generate spectral maps. A 57 mm×30 mm window within each sample was assessed and each spectral map included 220 measurement points.

Computational implementation of the proposed model was carried in MatLab (Mathworks, Inc) as a two-step process, each requiring curve fitting of experimental data. First, the signal was pre-processed to remove fluorescence background and then relevant segments of Raman spectra were modeled. Fluorescence is commonly removed by fitting the region of the spectra below distinctive Raman bands with low order polynomial function. Fluorescence was iteratively fitted with a fifth order polynomial and subsequently subtracted from the raw signal. In the second step, the vibrational modes of interest were approximated as a damped harmonic oscillator driven by a force whose profile follows a sinusoidal curve. According to the hydrodynamic theory, Raman lines naturally follow a Lorentzian profile. Thus the optimization function is the sum of Lorentzians. The trust region optimization model was employed for curve fitting of the Raman spectra. Conceptually, it is a maximum neighborhood method developed through interpolation between the Taylor series method and the gradient descent method. It sets a problem as the iterative solving of a set of nonlinear algebraic equations. However, if the initial estimate is too far from the optimum, the algorithm will not converge. Therefore the subset of the region of the objective function is defined and optimized first. The function is approximated with a simpler one which reasonably reflects the behavior of the original function in a neighborhood E around the point x. This neighborhood is referred to as the trust region. In essence, the trust region represents constraints derived from the underlying biochemistry of the specimen.

Collagen in the ECM of articular cartilage is predominantly type II (COL II), whereas due to practical considerations our model utilizes type I (COL I). The major difference between COL I and COL II is a 'phase shift' in their chains. In COL I the NH groups point counter-clockwise when viewed from the carboxyl ends of the chains, whereas in COL II the opposite is true. According to Rich and Crick, if an existing set of hydrogen bonds in COL I is broken, and each polypeptide chain rotated about its own axis by approximately n/3, the NH group would instead be attached to the carbonyl oxygen, forming the hydrogen bond. Illustration of the 'phase shift' between COL I and COL II can be found in. Consequently, Raman spectra of COL I and II are rather similar (FIG. 2). Further, the proposed cross-link (CxL) concentration assessment relies on quantification of the concentration pyridine aromatic rings, which are centerpieces of both pyridiniumCxLs induced by GA-fixation in COL I and hydroxylysylpyridinoline (PYD) CxLs that are present in the COL II of the ECM of articular cartilage. The Raman band associated with in-plane stretching of pyridine ring is observed at the same location in the spectra of COL I and COL II (FIG. 2c) as well as in articular cartilage explants. The ring is a prominent CxL residue found in fibrillar COLs and most connective tissues, except cornea and skin.

Collagen is a large molecule comprised of three polypeptide chains, which form a right-handed triple helix. Each of the chains contains multiple regions of repeating amino acid sequences (Gly—X—Y)n, where Gly is glycine and X and Y are often proline and hydroxyproline. FIG. 3 depicts typical Raman spectra of collagen type I (COL I) obtained from a thin film sample, superimposed with the spectra of GA-treated COL I. The dominant Raman band at the far right side of the spectrum, centered at 1669 $cm^{-1}$, is assigned to amide I and in COL I is mainly attributed to carbonyl stretching of the peptide bond in the Gly—X—Y tripeptide sequence. Two superimposed Raman bands in the center of the signal, with peaks at 1240 $cm^{-1}$ and 1268 $cm^{-1}$, respectively represent coupling of CN stretching with NH in-plane deformation, and are assigned to amide III. The peak at 1240 $cm^{-1}$ is associated with proline rich regions, whereas 1268 $cm^{-1}$ corresponds to proline poor regions, respectively. Amide I and amide III, together with C—C stretching of the backbone formed by the Gly—X—Y sequence found at 935 $cm^{-1}$, suggest an α-helix conformation. Vibrations of the proline ring, specifically C—C stretching, is attributed to Raman bands centered at 853 $cm^{-1}$ and 918 $cm^{-1}$, and the hydroxyproline ring gives rise to Raman band with peak at 875 $cm^{-1}$. The isolated Raman band located at 1030 cm-1 is associated with C—C stretching of aromatic pyridine ring.

GA treatment resulted in a shift of the amide I and amide III bands. The peak of the amide I band shifted to 1674 $cm^{-1}$, and bands attributed to Amide III became centered at 1235 $cm^{-1}$ and 1264 $cm^{-1}$, respectively. In the spectra of GA-fixed samples, a new band appeared at 865 $cm^{-1}$ which is attributed to COC symmetric stretching. This band is due to ether-type COC CxL, which is a result of the reaction of the GA aldehyde group with the carbonyl group of the peptide bond in COL. Newly formed ether-type bond weakens hydrogen bonds, producing conformational modifications of the protein structure, which are seen as Raman shifts of the amide I and amide III bands. Quaternary pyridinium compounds form stable CxLs in GA-fixed samples. The 1030 $cm^{-1}$ band is due to in-plane deformation of six-membered aromatic ring and is an indicator of the 1, 3, 5-substituted pyridine ring, similar to the CxLs of interest in articular COL.

Pyridinium-type CxLs in GA-fixed COL samples have a pyridine ring as their central feature whose vibrational modes are similar to monosubstituted six-membered rings. Similarly PYD, which is one of the major COL CxLs and is responsible for the tensile strength and structural integrity of cartilage ECM has a pyridine-like aromatic ring as its central chemical structure (FIG. 4a). Assessment of relative concentration of pyridine rings in articular cartilage thus can provide information about the concentration of PYR CxLs. Stable vibrational modes of pyridine consist of in-plane ring deformation and symmetric ring breathing modes (FIG. 4b). The former involves displacing alternate carbon atoms around the ring and is characterized by a rise of the 1030 $cm^{-1}$ band. The latter is attributed to symmetric ring stretching that involves all carbons and nitrogen moving in and out in unison. The Raman band associated with this mode is located at 992 $cm^{-1}$. The 1030 $cm^{-1}$ band is present in both purified COL (box II in FIG. 3) and bovine articular cartilage explants. Furthermore, there is no significant overlapping of the Raman band centered at 1030 $cm^{-1}$ and other bands in the COL spectra, which simplifies the analysis to some extent.

Quantification of the changes in the relative concentration of pyridinium-type CxLs was achieved via modeling of the experimental data, which enabled the analysis of changes in individual Raman bands due to GA-fixation. It is assumed that the relative concentration of the pyridine rings within the focal volume is proportional to the normalized integrated intensity of the Raman band associated with in-plane ring deformation. Modeling of the spectrum was needed to assess contributions of the individual bands to the complex signal that is comprised of a relatively large number of overlapping Raman bands. Subsequently, quantitative information about the particular Raman band of interest could be extracted from the model. By taking advantage of the additive property of the Raman signal, segments of interest in the COL Raman spectra (box I and box II in FIG. 3) can be seen as the sum of the individual bands. Therefore the optimization function, which is used to model the spectrum, is the sum of the functions describing individual bands. The concentration of CxLs is quantified as the area under the curve of the 1030 $cm^{-1}$ peak in the modeled spectrum, normalized by the area under the hydroxyproline curve assigned to COL. Normalization is necessary to avoid errors which could arise as a result of concentration-dependent changes, as done in FTIR studies. The trust region optimization model used for these analyses, is an adaptive method that utilizes a two-step approach in which the approximation model predicts the improvement of the system being optimized before resorting to a detailed model that confirms the validity of the initial approximation, followed by constrained variation of the trust region. The modeling enforces a locally constrained optimal step in the otherwise unconstrained approximate iteration. The underlying biochemistry, including the location of the peak assignments, helped to introduce appropriate constraints in the optimization model so that a unique solution could be obtained. This approach yields a unique solution when treating large numbers of varying parameters, while being sufficiently sensitive to capture subtle changes in the vibrational spectra that arise from the potentially modest changes in the crosslink density. Two segments of the spectrum have been modeled, and the resulting modeled spectrum closely matches experimental data (FIG. 5). From the first segment the integrated intensity of the hydroxyproline band has been extracted and used to normalize the integrated intensity of the band centered at 1030 cm$^{-1}$, which is associated with in-plane stretching of pyridine rings.

Spatially resolved characterization of the COL thin films was utilized for generation of spectral maps (FIG. 6). Each spectrum in the map was modeled as outlined above and the integrated intensity of the 1030 cm$^{-1}$ band was utilized as a parameter that represents CxL relative concentration. Each map depicted in FIG. 6 corresponds to a specimen subjected to GA fixation. In these maps it can be seen that an increase in the concentration of GA and prolonged exposure to GA both produce an increase in the relative concentration of pyridinium-type CxLs. Averaged values of CxL concentrations at different exposure times and GA concentrations are summarized in FIG. 7. COL thin films exposed to 0.05% GA experience a nearly linear increase in the relative CxL concentration, whereas specimens treated with 0.1% and 0.2% GA solution exhibit a higher rate of increase in the first hour of exposure, after which the increase rate slows down and becomes similar to that seen in samples fixed with 0.05% GA solution.

A collagen thin film model to simulate changes in relative crosslink concentration in extracellular matrix of an articular cartilage has been introduced. Samples were treated with varying concentrations of glutaraldehyde solutions at different exposure times to induce pyridinium-type crosslinks. These crosslinks are relevant to this model system as their centerpiece is the pyridine ring, which is also the central chemical compound of hydroxylysyl pyridinoline, a crosslink found in the extra cellular matrix of articular cartilage and whose degradation is associated with loss of its structural stability. A novel Raman-based method to quantitatively assess the concentration of pyridinium-type crosslinks has been proposed. The spectra of glutaraldehyde treated collagen matrix were acquired and relevant segments of the signal were modeled with an appropriate optimization function comprised of the sum of the Lorentz functions, each of which represents individual bands present in the complex signal obtained from the collagen sample. The known biochemistry of the target material provided appropriate constraints on the optimization algorithm to yield a unique solution, which was sufficiently sensitive to capture subtle alterations in the vibrational spectra. Normalized integrated intensity of the Raman band associated with the pyridinium-type cross-link was extracted from the resulting curve fit and its fluctuation as a function of exposure to glutaraldehyde was studied. Spatially resolved characterization of collagen thin films yielded spectral maps that showed an increase in the relative concentration of pyridinium-type crosslinks in collagen with prolonged exposure to glutaraldehyde solution. Future work envisions the application of the proposed model to cartilage explants and the validation of this method against available biochemical assays for quantification of crosslink concentrations.

Section A. Disclosure on Crosslinking of Corneal Tissue

Nearsightedness is a growing problem worldwide. Its incidence has doubled in past fifty years in United States and Europe, and is even more prevalent in East Asia. Although spectacles and contact lenses remain the most common means of vision correction, permanent correction of refractive errors, made possible with refractive surgeries, has emerged as an attractive alternative. However, refractive surgeries are invasive procedures that compromise corneal structure, and thus are subject post-surgical complications. Furthermore, these procedures are not available to patients with thin corneas, poor tear production and certain topographic abnormalities. In our prior work we have demonstrated viability of noninvasive vision correction. The proposed method relies on induction of a low-density-plasma in the focal volume which ionizes the surrounding molecules, and produce reactive oxygen species (ROS). When the treatment is applied onto corneal stroma, newly formed ROS interact with surrounding collagen fibrils to form crosslinks (CxLs). These CxLs 'pull' adjacent lamellae closer together, and locally densify laser irradiated stroma, effectively altering the overall corneal curvature. Adjustment of the corneal curvature changes eye's effective refractive power (ERP), and therefore can be used for vision correction. In this study, we are applying previously developed treatment modality on rabbit models in vivo to assess its safety and efficacy.

Laser treatment of the central region of cornea results in its flattening and amends the ERP of eye in such a way, that it could be used for treatment on myopia. The flattening is a product of highly localized changes in the mechanical properties, driven by laser induced CxLs, which selectively increase corneal rigidity. Interaction between the ultrafast laser pulses and the target biological media is confined to photochemical effects by restricting the ultrafast laser irradiation below the optical breakdown threshold. Further, the treatment regime is such that restricts appearance of damaging thermoacoustic and shock waves.

Figure 11:
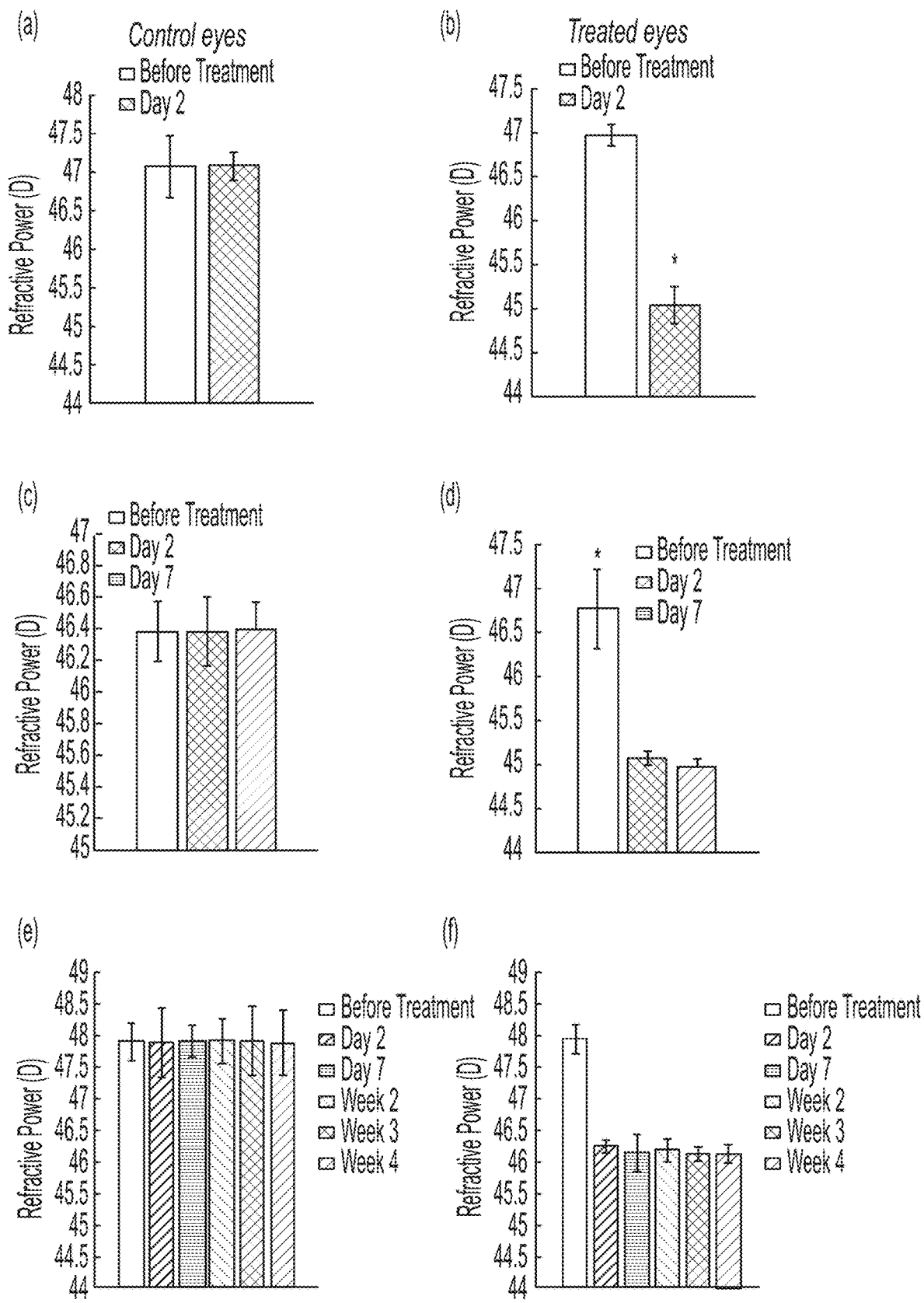
FIG. 11. Time-history of the treatment induced changes in live rabbit corneal effective refractive power (EPR) of: group 1 (a, b), group 2 (c, d), and group 3 (e, f). Untreated control eye (a, c, e) demonstrated that the ERP does not change in control eye, whereas the laser treatment decreases ERP, which remains stable (b, d, e) for one month after the procedure. *p<0.05: change of refractive power is statistically significant.

FIG. 11. Time-history of the treatment induced changes in live rabbit corneal effective refractive power (EPR) of: group 1 (a, b), group 2 (c, d), and group 3 (e, f). Untreated control eye (a, c, e) demonstrated that the ERP does not change in control eye, whereas the laser treatment decreases ERP, which remains stable (b, d, e) for one month after the procedure. *$p<0.05$: change of refractive power is statistically significant.

Corneal topography has been assessed after the treatment to evaluate changes of the eye ERP. In group 1, 48-hours after the treatment, observed average change of ERP in treated eyes was 1.74 diopters (FIG. 11a), relative to the pre-treatment value. The relative change of ERP in treated eyes of group 2 was 1.74 48-hours post-treatment, and 1.64 7-days after the treatment (FIG. 11b). No significant change of ERP has been observed in control eyes of both groups during the same period (FIG. 11c,d). Stability of the treatment produced changes in ERP has been monitored in the third group of animals (FIG. 11e,f). Treatment amended ERP has been stable for one month after the treatment, with relative change of EPR in treated eyes being about 1.94 diopters. The change of the ERP is statistically significant, albeit smaller than one observed in porcine eyes treated ex vivo. This is a reasonable result, given the anatomical and morphological differences between eyes of these two species.

Figure 12:
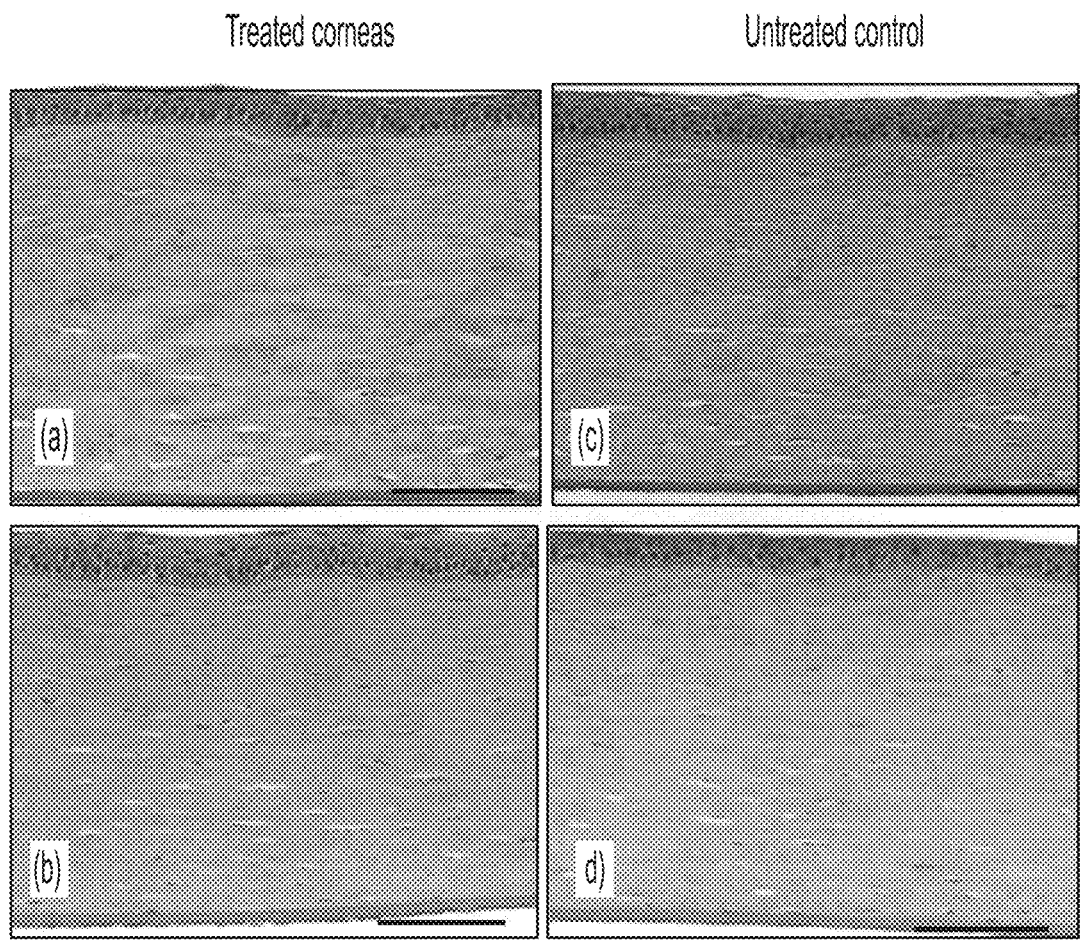
FIG. 12. Histological sections of haematoxylin-eosin (H&E) stained rabbit corneas: (a) two days post treatment; (b) seven days post-treatment; (c) and (d) corresponding untreated controls. Scale bar 100 μm.

FIG. 12. Histological sections of haematoxylin-eosin (H&E) stained rabbit corneas: (a) two days post treatment; (b) seven days post-treatment; (c) and (d) corresponding untreated controls. Scale bar 100 μm.

Hematoxylin—eosin (H&E) stained histological sections of corneas obtained at 48-hour post-treatment checkpoint and in 1-week follow-up show no difference in corneal structure when compared against the control samples (FIG. 12). There is no damage caused by the laser treatment to the epithelial, stromal and endothelium layers. Specifically, no wound and wound healing response, as seen in refractive surgeries, can be observed, nor presence of collagen disorganization, epithelial cell and stromal edema, intra-stromal vacuole formation and endothelial cell detachment, all of which are associated with thermal damage of stromal tissue.

Crosslinking of the corneal stroma in the presented study is carried out through formation of free radicals, which have potential to cause cell damage. For instance both, in vitro and in vivo studies of cytotoxicity of the riboflavin/UVA procedures showed that UV light collagen crosslinking in presence of riboflavin leads to immediate loss of the stromal keratocytes within the entire volume of the affected stroma. Although repopulation of the corneal stroma with activated keratocytes can take up to 6 months, the treatment is mostly considered safe for humans, unless corneas are thinner than 400 µm. In such a case, the main safety concern is associated with the endothelial damage which has also been reported in both in vivo and in vitro studies. Endothelium of the healthy cornea plays a key part in maintaining corneal hydration and transparency via the active sodium—potassium adenosine triphosphatase (ATPase) and the bicarbonate-dependent magnesium ATPase ionic pumps. The corneal endothelial cells are unable to replicate compensation is possible only by sliding. Decrease of the cell density below the critical limit leads to dysfunction of endothelial barrier and can result in loss of vision. Clinical studies have shown that the endothelium in human corneas thinner than 400 µm is susceptible to the riboflavin/UVA treatment related toxicity, which therefore restricts its usage. On the other hand, the present procedure is wavelength independent, and thus the treatment can be achieved with an ultrafast laser operating in infrared frequency domain, so that damaging effects of UV radiation are avoided.

Confocal laser scanning microscopy (CLSM) images of rabbit eyes have been obtained immediately after the euthanasia (groups 1 and 2) and in vivo (group 3). The distance between two consecutive imaged planes was 2 µm for epithelium and stromal keratocyte network. The monolayer of endothelial cells was imaged separately. Comparison of CLSM images of intact and laser treated rabbit eyes show no significant difference between their respective cellular structure (FIG. 13), thus implying that the laser irradiation induces no damage to the cellular components. Furthermore, CLSM images of the epithelial layer, stromal keratocyte network and endothelium are comparable with those reported in other studies. CLSM images of the endothelium (FIG. 13$m$-$r$) reveal no difference in cell shape and density when treated eyes are compared against paired controls.

Figure 13:
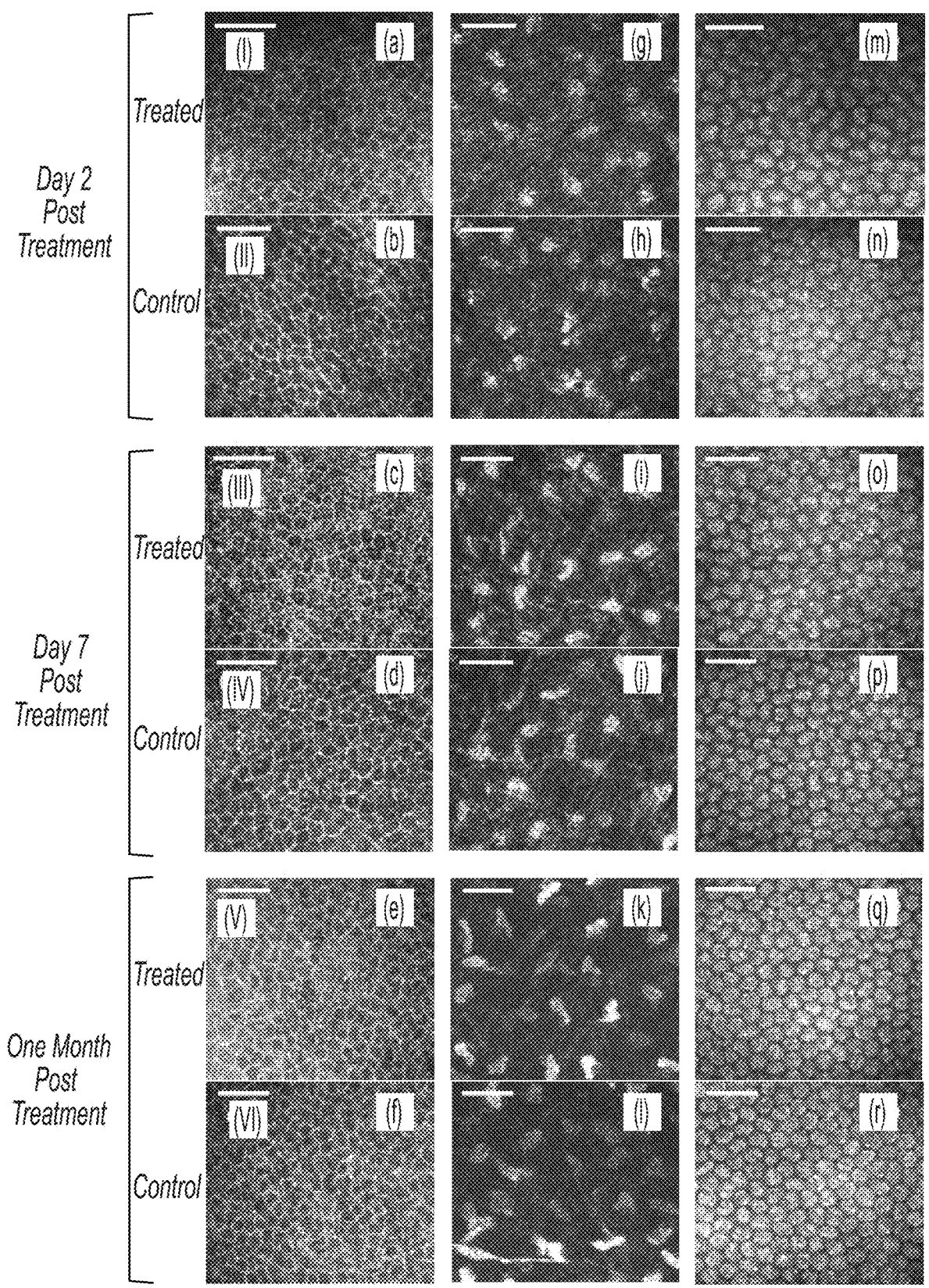
FIG. 13. Representative images of the in vivo confocal microscopy of the laser treated (column I, III and V) and control (rows II, IV and VI) rabbit eyes obtained 48 hours (rows I and II), 7-days (rows III and IV) and one month (rows V and VI) after the treatment. (a~f)—corneal epithelium; (g~l)— keratocytes network; (m~r)—corneal endothelium (scale bar=50 μm).

FIG. 13. Representative images of the in vivo confocal microscopy of the laser treated (column I, III and V) and control (rows II, IV and VI) rabbit eyes obtained 48 hours (rows I and II), 7-days (rows III and IV) and one month (rows V and VI) after the treatment. (a~f)—corneal epithelium; (g~l)—keratocytes network; (m~r)—corneal endothelium (scale bar=50 µm).

Quantitative analysis of keratocytes (FIG. 14$a$) and endothelium cells (FIG. 14$b$), performed by using FIJI imaging software, shows similar cell count in both, treated and control eyes. Density of the keratocytes 48-hours post-treatment (39464.29±2288.57 cells/mm$^3$) was similar to untreated controls (39523.82±5868.68 cells/mm$^3$). The keratocyte density in both treated and controlled eyes remained stable up to one month after the treatment. The endothelium cell counts 48-hours post-treatment were 2925.00±64.14 cells/mm$^2$ and 2908.33±101.04 cells/mm$^2$, for laser irradiated corneas and untreated controls, respectively. There was no change in the endothelium cell density on day 7 and one month post-treatment. Observed counts of keratocytes and endothelium cells were within the normal range.

Figure 14:
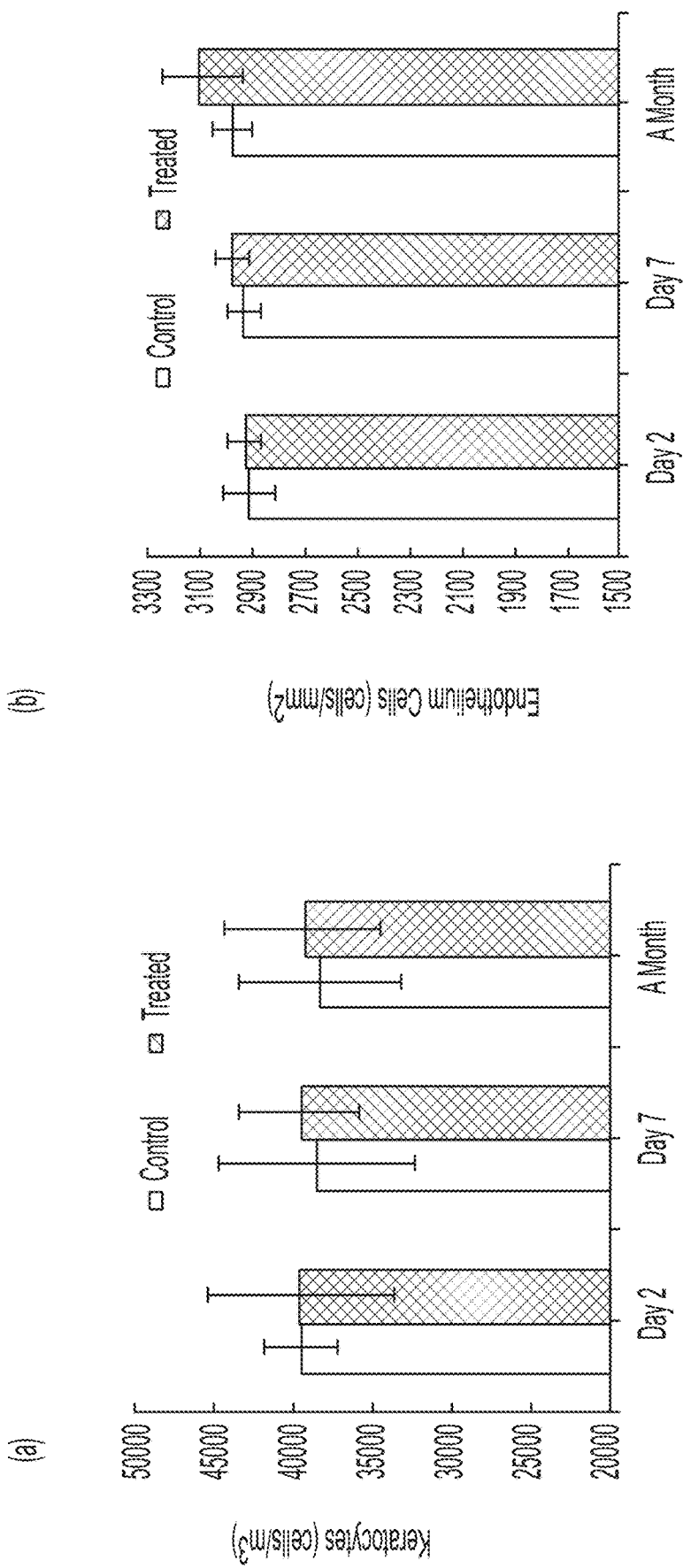
FIG. 14. In vivo rabbit corneal keratocytes (a) and endothelium cells (b) density on Day 2, Day 7 and a month after the laser treatment.

FIG. 14. In vivo rabbit corneal keratocytes (a) and endothelium cells (b) density on Day 2, Day 7 and a month after the laser treatment.

Ultrafast laser treated regime that restricts interaction between the laser pulses and biological media to photochemical effects via imparting low-density-plasma within the focal volume, recently discovered by our group, has been applied as means to amend effective refractive power in rabbit models. As such, the proposed treatment serves as paradigm for non-invasive vision correction. Presented study, which is a natural extension of our prior work on ex vivo porcine eyes, has demonstrated that the proposed treatment modality is safe and effective. No negative side effects associated with existing techniques, refractive surgeries and riboflavin/UVA light crosslinking have been observed. The method is capable to simultaneously introduce crosslinks to enhance the corneal mechanical properties, similarly to riboflavin/UVA but without depopulating stromal keratocytes and damaging endothelium, and to noninvasively adjust corneal curvature, the effect previously reserved for refractive surgeries. The future studies will focus on development of governing relationships that connect full-field deformation of the corneal tissue with the CxL density toward establishing means to effectively control the process, further study longevity of the induced changes, and finally to expand the laser-tissue interaction paradigm to other collagen rich tissues in need of enhancement of their mechanical properties.

Methods

Animals. In vivo experiments were performed on young adult Dutch Belted rabbits, each weighting 1.8-2.0 kg. Rabbits are commonly used as models for correction of refractive errors, despite anatomic differences between human and rabbit eyes, such as lack of Bowman's layer. Animals were delivered to Columbia University's Institute of Comparative Medicine (ICM) housing facility one week prior to the laser treatment, which allowed animals enough time to acclimate to the new environment. Experimental protocol, as well as pre- and post-treatment handling procedure, has been reviewed and approved by Institutional Animal Care and Use Committee of Columbia University. Total of twelve animals used in the study were divided into three groups; the first group of animals (n=3) has been sacrificed and eyes enucleated 48-hours post laser treatment to investigate acute effects of laser irradiation. The second group (n=3) was euthanized after 1 week, which would allow eyes to undergo at least partial healing in case the laser produced any damage to the tissue. In this group, the eye refractive power has been examined 48-hours post-treatment as well. The last group of animals (n=6) has been monitored to investigate long-term stability of the induced refractive power changes. Animals were euthanized 48 hours (group 1) and seven days (group 2) post-treatment, by intravenous injection of pentobarbital (100 mg/kg) through marginal ear vein. The cornea, retina and lens were then isolated, fixed with 10% formalin overnight, desorbed with 70% alcohol for 24 hours and sent to Columbia Medical Center Histology Service for histological staining. Briefly, samples were embedded in paraffin wax and cut into 5 µm thickness slices through cross section and stained with hematoxylin and eosin. Histological slices were imaged by a VHX 5000 digital microscope (Keyence Corporation, NJ) and processed by ImageJ.

Treatment. Prior to the treatment, gross examination and slit-lamp evaluation of animal corneas was performed by a veterinarian to ensure there are no abnormalities or eye injuries. Rabbits were anesthetized with an intra-muscular injection of ketamine (35 mg/kg) and xylazine (5 mg/kg), placed on a warm heating pad and monitored until fully unconscious. The depth of anesthesia has been confirmed by lack of a pedal and ear pinch reflex. Anesthetized rabbit was gently immobilized with a custom-built, heavily padded holder (FIG. 1a, b). The faced-up eye was treated, and the faced-down eye was used as untreated control. Proparacaine (0.5% ophthalmic solution) drops were applied onto to the treated eye as local anesthesia, which was followed by application of GenTeal water based gel (Novartis, Alcon, Inc, TX, USA) to prevent corneal dehydration. GenTeal gel has been applied onto both eyes, and replenished during the procedure, as needed. Treated eye was gently pressed with a cover slip to ensure even volumetric application of laser pulses. The laser treatment protocol was based on the procedure developed in our prior study, in which porcine eyes were treated ex vivo. Nd:Glass ultrafast laser (Hi-Q Laser, Austria) with 99 fs laser pulse duration and 52 MHz repetition rate delivering pulses at 1059 nm wavelength was utilized for the treatment. The laser beam was focused via high numerical aperture objective (Zeiss, Plan Neofluar 40x/0.6) into the desired volumetric zone of the cornea. The average laser power at the focal point was about 60 mW. The objective was mounted onto a custom built 3-axis motion system consisting of three translational stages (PT1, Thorlabs, Newton, N.J.) coupled with motorized actuators (Z825B, Thorlabs, Newton, N.J.). A number of optical components such as mirrors and lenses were mounted onto the motion system as well to steer the laser beam into the back aperture of the objective. Laser pulses were rasterized by moving the objective in a x-y plane such that the laser path followed a zigzag pattern, resulting in a treatment of a circular planar surface (Ø 5 mm) at specific depth (FIG. 1c). The treatment was repeated at different depths, effectively inducing 'treatment layers'. In presented experiments five treatment layers parallel to the superficial surface were applied with 50 μm distance between the consecutive layers, similarly to our previous study. Such a treatment (FIG. 15c) results in corneal flattening. Rabbits were returned to ICM housing facility immediately after the treatment.

Figure 15:
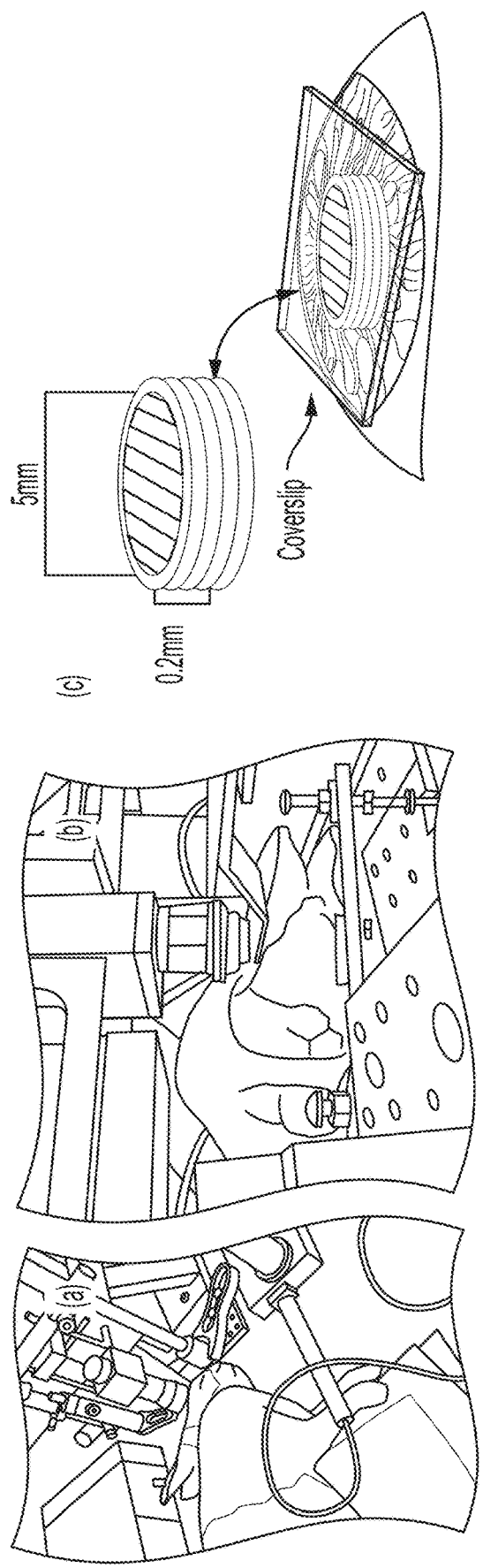
FIG. 15. Experimental Setup for live animal treatment (a) and (b). Rabbits were deep anesthetized and placed in a customized holder. Treatment pattern (c) consists of applying laser pulses such that the laser path follows a zigzag pattern in a circle with Ø 5 mm, thus treating a planar surface at the specific depth level. The treatment is repeated at five different depths, effectively inducing 'treatment layers'. Multiple treatment layers parallel to the superficial surface were applied with 50 μm distance between two consecutive planes.

FIG. 15. Experimental Setup for live animal treatment (a) and (b). Rabbits were deep anesthetized and placed in a customized holder. Treatment pattern (c) consists of applying laser pulses such that the laser path follows a zigzag pattern in a circle with Ø 5 mm, thus treating a planar surface at the specific depth level. The treatment is repeated at five different depths, effectively inducing 'treatment layers'. Multiple treatment layers parallel to the superficial surface were applied with 50 μm distance between two consecutive planes.

Figure 16:
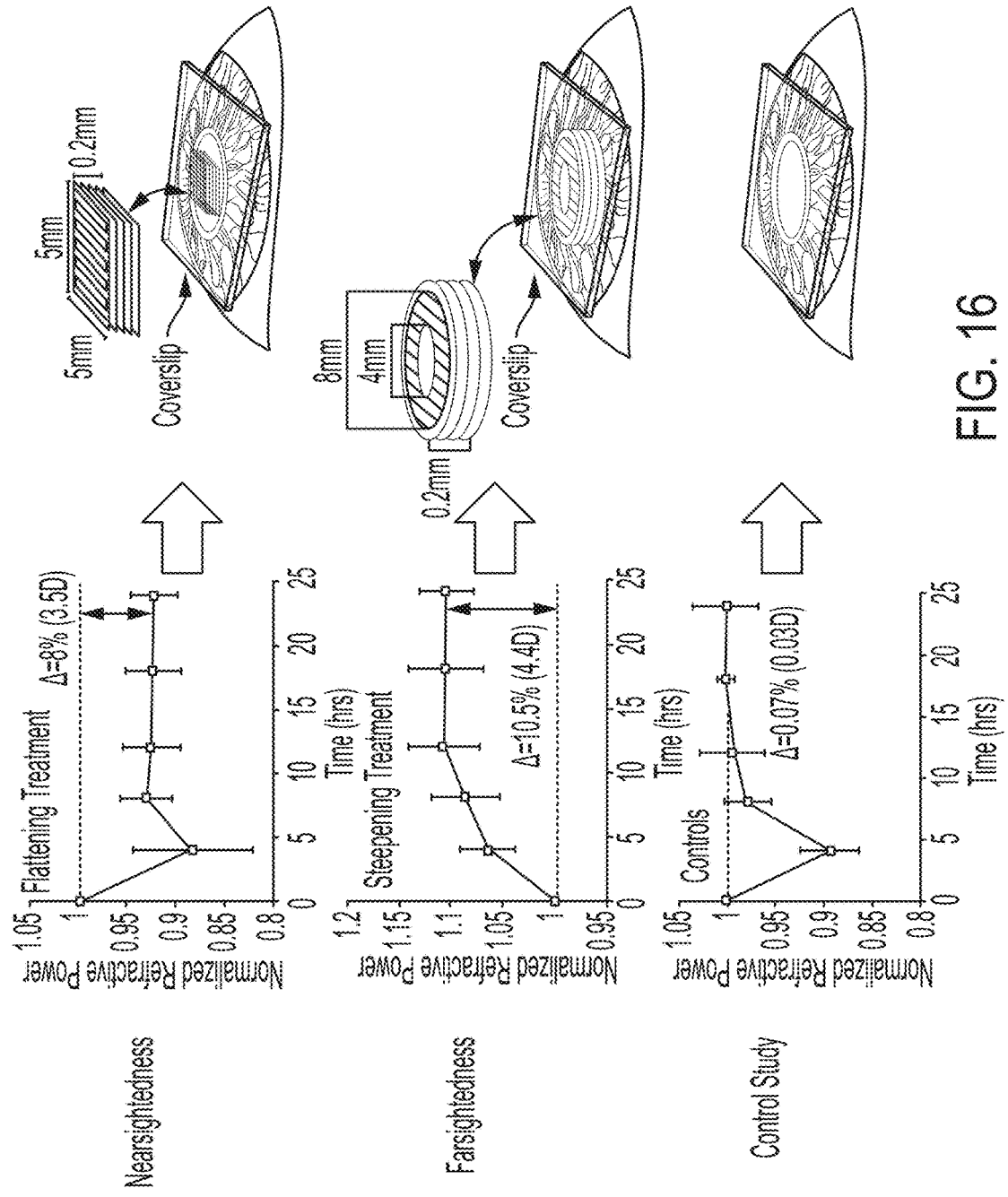
FIG. 16 shows correction of refraction errors.

FIG. 16 shows correction of refraction errors

Topography. Topographic measurements of the entire corneal area were performed before the treatment, 48 hours after the treatment (groups 1, 2 and 3), seven days after the treatment (groups 2 and 3), and then once per week (group 3) to assess the effects of laser light-induced corneal crosslinking to change of eye refractive power. Measurements of the corneal topography immediately after the treatment, to compare results against the previous ex vivo study, produced highly irregular pattern and abnormal results due to anesthesia driven, significant drop of the intraocular pressure, and as such were omitted from this report. Topographic measurements were performed using Eyesys Vista non-contact eye-topographer (EyeSys Vision Inc, Houston, Tex.).

Confocal Laser Scanning Microscopy (CLSM). Confocal laser scanning microscopy (CLSM) was employed to evaluate corneal tissue at the cellular level. CLSM imaging utilized HRT3-RCM laser-scanning system (670 nm laser beam, Heidelberg Engineering, Dossenheim, Germany) equipped with a 63x/0.95 NA water immersed objective (Zeiss, Germany). Imaging was performed immediately after euthanasia for groups 1 and 2 (48 hours after the treatment and 7 days after the treatment, respectively) and in vivo for group 3 (28 days after the treatment). A disposable sterile plastic cap has been placed on the objective to keep the distance between the corneal surface and objective. Animals were placed on an in house-built holder during the process with the eyelids of the imaged eye gently pulled by hand. A GenTeal water based gel was applied as a coupling medium. The entire corneal volume was scanned and recorded with the optical section through epithelium, stroma and endothelium.

Porcine corneas were cultured post treatment to assess the effects of the femtosecond oscillator irradiation. Specifically, it is of interest to evaluate whether there is any degradation occurring in the crosslinked layers of stromal matrix as well as potential adverse effects to cellular components. Cultured corneas were evaluated at 1-day and 7-day time points, which is consistent with earlier studies in which riboflavin soaked corneas were crosslinked with UVA light.

Figure 17:
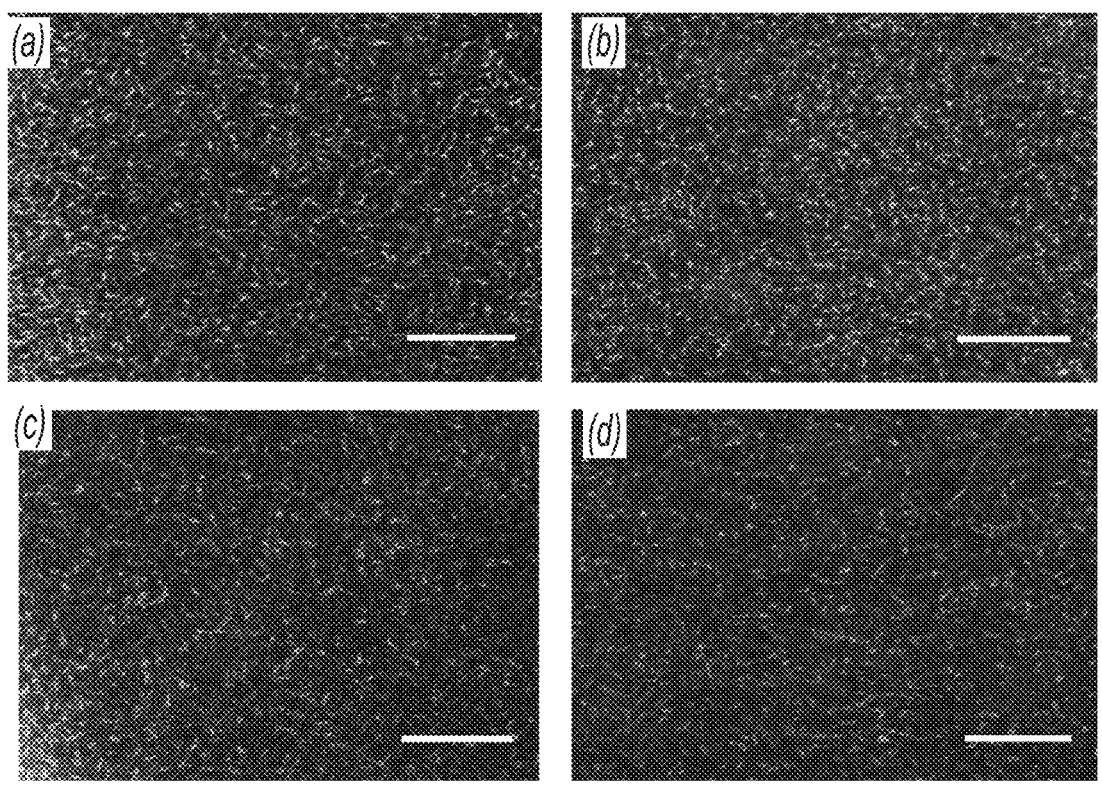
FIG. 17. Live/Dead staining of corneal punches: (a) control and (b) laser treated at 24 h; (c) control and (d) laser-treated at 1-week. Live cells are marked green and dead cells are marked red. Scale Bar: 200 μm.

FIG. 17. Live/Dead staining of corneal punches: (a) control and (b) laser treated at 24 h; (c) control and (d) laser-treated at 1-week. Live cells are marked green and dead cells are marked red. Scale Bar: 200 μm.

Methods. Freshly harvested porcine eyes were treated with the femtosecond oscillator, following the procedure outlined in the methods section. Total of 40 eyes were used in the study, 20 of which were treated, and they were paired with 20 controls. After the laser treatment, eyes corneal topography has been monitored for 24 hours under controlled conditions. After the topography observation period, eyes were removed from custom built eye holders, rinsed with 20 ml of sterile phosphate balanced solution (PBS) three times, immersed into 20 ml 3% polyvinylpyrrolidone-iodine (PVP-I) solution for about 1 minute and rinsed again with sterile PBS three times. After second rinsing, corneas were dissected from the eye together with about 1 mm thick scleral rim. Half of the samples were immediately examined (24 hours time point), and the other half placed into sterile cultivation vessel (Fisher Scientific, CAT #08722E). The vessel was filled with 8 ml customized incubation media that consists of low glucose Dulbecco's Modified Eagle Medium (Thermofisher) with 8% fetal bovine serum and appropriate antibody. Corneas were cultivated at 37° C. in a tissue culture incubator (Thermo Scientific Series 8000 DH, Waltham, Mass.). Cell viability (Live/Dead Assay Kit, Invitrogen) in the corneal stroma has been assessed for both 24 hours and 1-week time points after the treatment. 5 mm-diameter cylinders were punched out from the central part of corneas and assessed with confocal microscopy (Olympus Fluoview FV1000, Waltham, Mass.). The images were taken from the anterior side of the corneal samples, roughly in the middle of the sample thickness. In addition to cell viability, standard histology characterization has been performed on corneas at 24 hours and 1-week time points after the treatment, respectively. Corneas were fixed with 10% formalin overnight, desorbed with 70% alcohol for 24 hours and sent to Columbia Medical Center Histology Service for histological staining. There samples were embedded in paraffin wax, cut into 5 μm thick slices and stained with hematoxylin and eosin (H&E).

Figure 18:
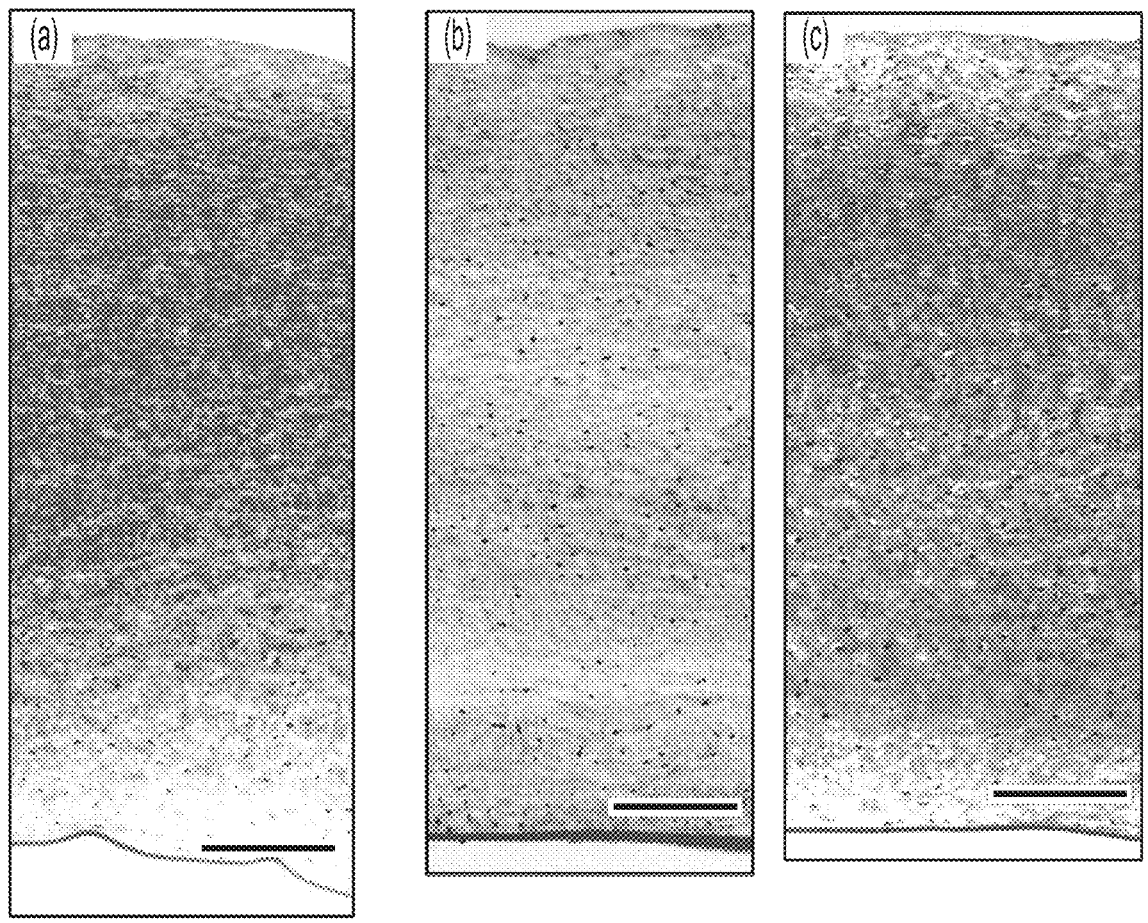
FIG. 18 (above). hematoxylin and eosin (H&E) stained histological cross-sections of (a) untreated control after 1-week in situ incubation; femtosecond laser irradiated porcine corneas after (b) 24-hour and (c) 1-week in situ incubation. Blue dots represent keratocytes3,4. Scale bar: 100 μm.

Results and Discussion. Confocal images of samples stained with live/dead assay kit demonstrated no evidence of viability loss 24 hours after treatment (FIG. 1a,b). For additional specimens, maintained for 1 week in the culture after the treatment, cell FIG. 18 (above). hematoxylin and eosin (H&E) stained histological cross-sections of (a) untreated control after 1-week in situ incubation; femtosecond laser irradiated porcine corneas after (b) 24-hour and (c) 1-week in situ incubation. Blue dots represent keratocytes. Scale bar: 100 μm viability was similarly maintained when compared against untreated controls (FIG. 1c,d). These results demonstrate that the laser treatment does not compromise cell viability for up to one week, as we have not observed significant post-treatment keratocytes depopulation in corneal stroma of treated samples. However, qualitative observation of the control and post treatment confocal images (FIG. 1) reveals that the cell density in treated samples is higher than in control specimens. This observation is corroborated by examination of tissue H&E stained slides (FIGS. 2, 3). Although H&E stained corneal sections of the femtosecond laser treated eyes show no significant alteration in stromal structure and endothelium integrity when compared against the untreated control (FIG. 2), it has been observed that treated anterior segments of corneas remain populated with keratocytes 24 hours post-treatment, as well as after being incubated in tissue culturing medium for 7 days at 37° C. (FIG. 3). Specifically, after 1-week incubation period, keratocytes remain present in the treated samples within the entire cross-section (FIG. 2c) whereas in the cultured control corneas keratocytes remain present only in the posterior regions (FIGS. 2a, 3).

Figure 19:
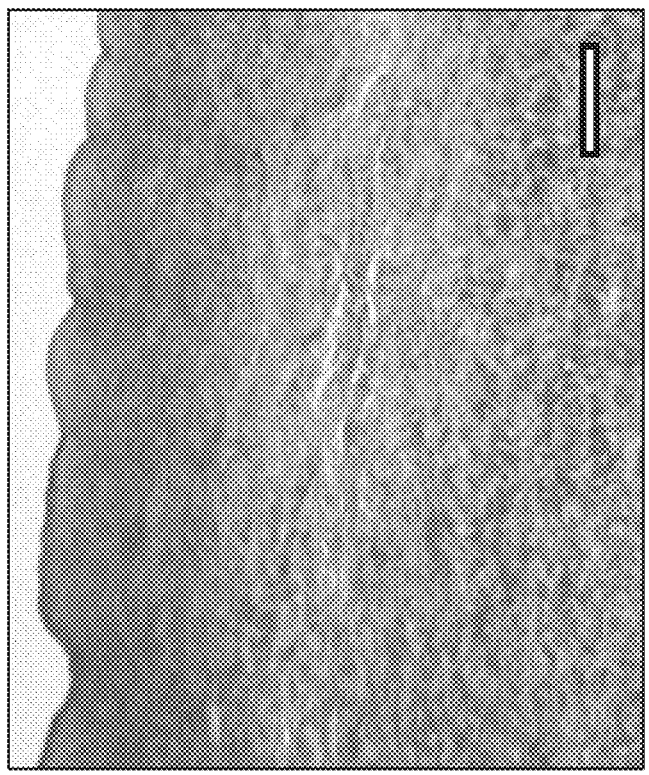
FIG. 19. hematoxylin and eosin (H&E) stained histological cross-sections of anterior portion of (a) femtosecond laser irradiated porcine corneas and (b) untreated control. Both after 1-week in situ incubation. Blue dots represent keratocytes3,4. Scale bar: 100 μm.
Figure 19:
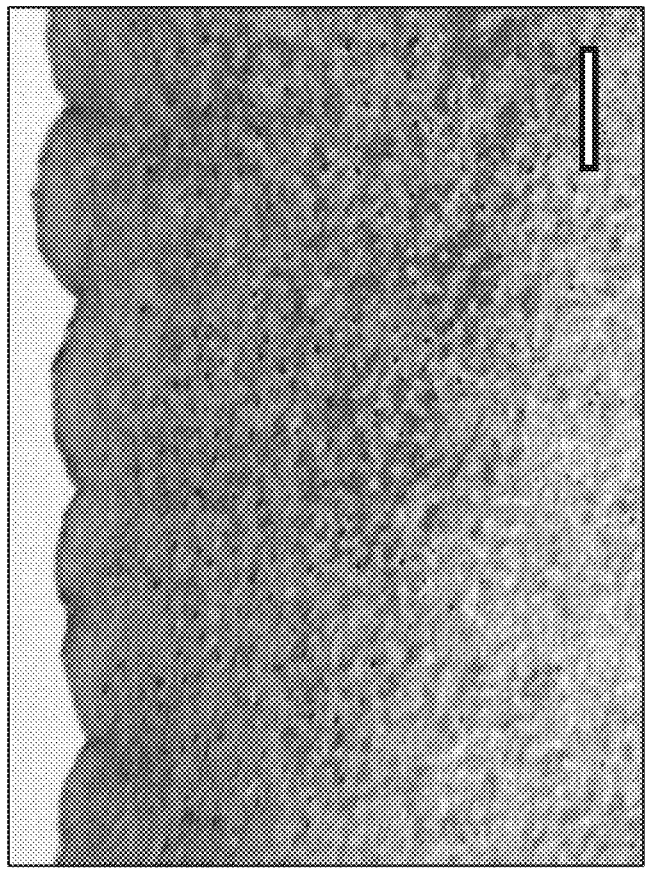

FIG. 19. hematoxylin and eosin (H&E) stained histological cross-sections of anterior portion of (a) femtosecond laser irradiated porcine corneas and (b) untreated control. Both after 1-week in situ incubation. Blue dots represent keratocytes. Scale bar: 100 μm The finding is rather unusual as debriding of the corneal epithelium results in apoptosis driven keratocyte depopulation. In presented study corneal epithelium has been removed because most samples suffered superficial damage due to handling in abattoir, and therefore absence of keratocytes in anterior stroma was expected. Prior reports suggest that the epithelial-stromal apoptosis serves as antiviral response mechanism to limit proliferation of pathogens such as herpes simplex from injured corneal epithelium to the stromal tissue Similar disappearance of keratocytes in anterior stroma has been observed after photorefractive keratectomy (PRK) procedure, in which scraping of epithelium is followed by excimer laser-assisted photoablation of corneal stroma toward correction of refractive errors. It has been hypothesized that damaged epithelial cells release interleukin-1 (IL-1) into the corneal stoma, which regulate keratocyte apoptosis. In normal homeostasis IL-1 maintains tissue organization through apoptotic and possibly negative chemotactic effects on adjacent keratocytes. However, its effect on individual keratocyte is a function of localized concentration, and if lethal level has not been reached, the keratocyte will respond with negative chemotaxis rather than undergo apoptosis. In the presented experiments, epithelium has been scrapped off the porcine eyes prior to the laser treatment, which should have triggered release of IL-1 into the corneal stroma. However, large scale apoptosis of keratocytes in anterior stroma has not been observed. We may speculate that either propagation of IL-1 has been retarded by the treatment or cell-cell interactions have been modulated, however additional studies are needed to investigate this matter. Follow up study has potential to open a new avenue in understanding of pathophysiologic keratoconus development mechanism.

Figure 20:
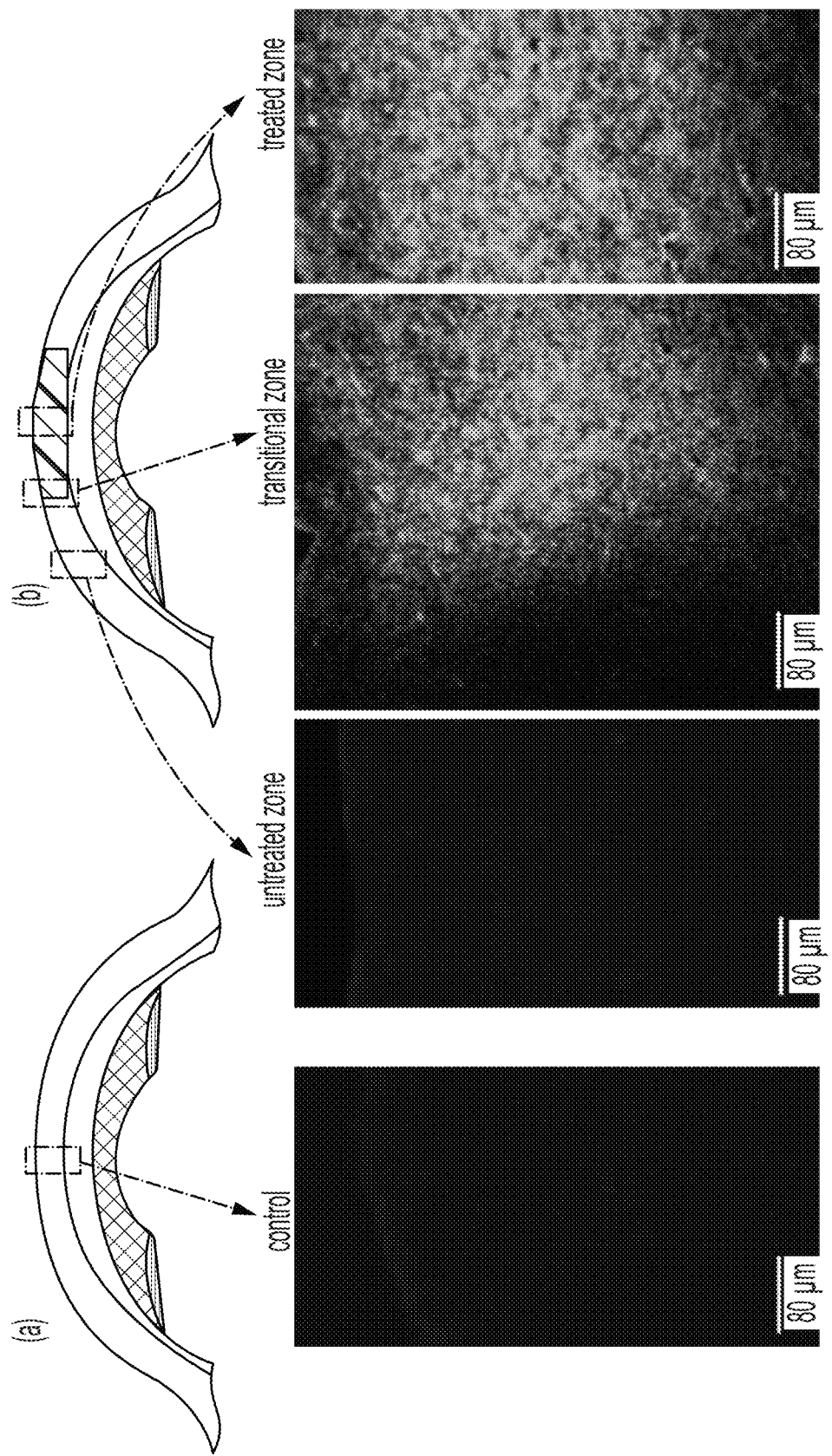
FIG. 20 Two-photon fluorescence (TPF) images of (a) control and (b) laser treated cross sections of porcine eyes. Three regions are imaged in the treated eye untreated region (left) transitional region (middle) central region (right) similarly to the procedure performed on eyes ex vivo (shown in the main body of the study); Control sample and the untreated region of the laser irradiated specimen after one week in culture ex vivo study show approximately the same crosslink density when compared with the 24 hours ex vivo study. The one week cultured samples showed a relative larger laser irradiated region, which is due to swelling of the corneal tissue after one week of culturing.

Analogously to characterization of cross-link density shown in the main text of the study, two-photon fluorescence FIG. 20 Two-photon fluorescence (TPF) images of (a) control and (b) laser treated cross sections of porcine eyes. Three regions are imaged in the treated eye untreated region (left) transitional region (middle) central region (right) similarly to the procedure performed on eyes ex vivo (shown in the main body of the study); Control sample and the untreated region of the laser irradiated specimen after one week in culture ex vivo study show approximately the same crosslink density when compared with the 24 hours ex vivo study. The one week cultured samples showed a relative larger laser irradiated region, which is due to swelling of the corneal tissue after one week of culturing.

(TPF) imaging has been utilized to visualize laser-induced changes in crosslink density in the treated parts of cultured porcine corneas. The structural difference between control and treated regions of the cultured corneas is similar to ones observed in ex vivo study (please see main body of the study), indicating that induced crosslinks are stable 1-week after the treatment. There is a difference in the size of affected region in cultured samples, which attributed to swelling of the corneal tissue after being 7-days in the culture.

Histological examination of the treated cornea has shown that the proposed laser treatment does not induce adverse effects on the stromal tissue. No collagen disorganization, stromal edema, intra-stromal vacuole formation or endothelium detachment has been observed. Density of induced cross-links appears to be stable after corneas being in culture for one week. Furthermore, it has been observed that the treatment retards injury induced apoptosis of stromal keratocytes, which may provide a new avenue in understanding of keratoconus, a corneal disease characterized by degradation of stromal structural integrity that results in diminishing of corneal mechanical properties, myopia, irregular astigmatism and loss of visual acuity. Although it is known that crosslinking enhances mechanical properties of cornea and thus stabilizes keratoconic eyes, the pathophysiology of keratoconus is not fully understood. However, corneal fibroblasts in keratoconic eyes do have four times more Il-1 receptors than ones seen in normal eyes. Whereas Il-1 plays a balancing role in normal homeostasis by regulating keratocyte proliferation and apoptosis, it is indeed possible that this balance is disrupted in keratoconic eyes, which experience keratocyte loss over extended periods of time. Presented study provided clues that crosslinking of keratoconic eyes provides benefits on cellular level in addition to stabilization of their mechanical properties.

What is claimed is:

1. A method of altering optical characteristics of a cornea, the method comprising:
   placing a transparent plate into contact with an outer surface of the cornea;
   applying a positive pressure with the transparent plate against the outer surface of the cornea;
   focusing a femtosecond laser onto a focal volume at a depth within stroma of the cornea;

emitting laser pulses from the femtosecond laser at an infrared wavelength;

irradiating the stroma of the cornea through the transparent plate by the emitted laser pulses;

during the emitting, scanning a focus point of the femtosecond laser in a plane parallel to the transparent plate and along a scanning pattern; and after the emitting, removing the transparent plate, wherein no photosensitizer is added to the cornea, the emitted laser pulses induce a low-density-plasma in the focal volume, the low-density-plasma ionizes surrounding molecules and produces reactive oxygen species, and the reactive oxygen species interact with collagen fibrils within the stroma to form collagen crosslinks.

2. The method of claim 1, wherein
an energy and power output of the femtosecond laser are adjusted by a pulse width, a selected wavelength, a focus region, and an intensity to prevent cell death greater than 50% in treated tissue.

3. The method of claim 2, wherein
any combination or subcombination of the energy and power output, pulse width, selected wavelength, focus region, and intensity is adjusted to cause crosslinking without optical breakdown.

4. The method of claim 1, wherein the scanning pattern is a square or circular pattern over a region of the cornea.

5. The method of claim 4, further comprising:
diagnosing a vision correction which would be corrected by flattening the cornea to decrease its refractive power.

6. The method of claim 5, wherein the cornea is a part of a living eye.

7. The method claim 1, wherein the scanning pattern is an annular pattern over a region having an outer diameter of the region and an inner diameter of the region.

8. The method of claim 7, wherein the outer diameter and the inner diameter are in a ratio of 2.5:1 to 1.5:1.

9. A method of altering optical characteristics of a cornea, the method comprising:

placing a transparent plate into contact with an outer surface of the cornea;

applying a positive pressure with the transparent plate against the outer surface of the cornea;

focusing a femtosecond laser onto a focal volume at a depth within stroma of the cornea;

emitting laser pulses from the femtosecond laser at an infrared wavelength;

irradiating the stroma of the cornea through the transparent plate by the emitted laser pulses;

during the emitting, scanning a focus point of the femtosecond laser in a plane parallel to the transparent plate and along a scanning pattern that is an annular pattern over a region having a ratio of 2:1 of an outer diameter of the region to an inner diameter of the region; and after the emitting, removing the transparent plate, wherein no photosensitizer is added to the cornea, the emitted laser pulses induce a low-density-plasma in the focal volume, the low-density-plasma ionizes surrounding molecules and produces reactive oxygen species, and the reactive oxygen species interact with collagen fibrils within the stroma to form collagen crosslinks.

10. The method of claim 9, further comprising:
diagnosing a vision correction which would be corrected by steepening a curvature of the cornea to increase a refractive power of the cornea.

11. The method of claim 10, wherein the cornea is a part of a living eye.

12. A method of altering optical characteristics of a cornea, the method comprising:

placing a transparent plate into contact with an outer surface of the cornea;

applying a positive pressure with the transparent plate against the outer surface of the cornea;

repeating for each depth of a plurality of different depths within stroma of the cornea the steps of
focusing a femtosecond laser onto a focal volume at said each depth,
emitting laser pulses from the femtosecond laser at an infrared wavelength,
irradiating the stroma of the cornea through the transparent plate by the laser pulses emitted by the femtosecond laser, and
during the emitting, scanning a focus point of the femtosecond laser in a plane parallel to the transparent plate and along a scanning pattern; and after the repeating, removing the transparent plate, wherein no photosensitizer is added to the cornea, the laser pulses emitted during the repeating induce a low-density-plasma in the focal volume, the low-density-plasma ionizes surrounding molecules and produces reactive oxygen species, and the reactive oxygen species interact with collagen fibrils within the stroma to form collagen crosslinks.

13. The method of claim 12, wherein the femtosecond laser emits laser light of wavelength 700-750 nm.

14. The method of claim 13, wherein the laser light is of wavelength 710 nm.

15. The method of claim 12, wherein the plurality of different depths is 2 to 10 depths.

16. The method of claim 15, wherein the plurality of different depths is 3 to 7 depths.

17. The method of claim 15, wherein the plurality of different depths is 5 depths.

18. The method of claim 12, wherein the plurality of different depths overlap completely.

19. The method of claim 12, wherein the plurality of different depths taken together are within a total depth of 0.1-0.4 mm.

20. The method of claim 19, wherein the plurality of different depths taken together are within the total depth of 0.2 mm.

21. The method of claim 12, wherein adjacent ones of the different depths are separated by 20-80 μm.

22. The method of claim 12, wherein
a surface is treated at each of the different depths, and
each surface has an area of 5-50 mm$^2$.

23. The method of claim 22, wherein each surface has an area of 10-40 mm$^2$.

24. The method of claim 23, wherein each surface has an area of 15-30 mm$^2$.

25. The method of claim 12, wherein each surface has an annular shape having an outer diameter and an inner diameter.

26. The method of claim 25, wherein the outer diameter and the inner diameter are in a ratio of 2.5:1 to 1.5:1.

27. The method of claim 26, wherein the outer diameter and the inner diameter are in a ratio of 2:1.

* * * * *